US007026299B2

(12) United States Patent
Li et al.

(10) Patent No.: US 7,026,299 B2
(45) Date of Patent: Apr. 11, 2006

(54) CONNECTIVE TISSUE GROWTH FACTOR-2

(75) Inventors: Haodong Li, Gaithersburg, MD (US); Mark D. Adams, Cleveland Heights, OH (US); Valérie Calenda, Strasbourg (FR); Virginie Fataccioli, Thiais (FR)

(73) Assignees: Human Genome Sciences, Inc., Rockville, MD (US); Transgene S.A., Strasbourg (FR)

( * ) Notice: Subject to any disclaimer, the term of this patent is extended or adjusted under 35 U.S.C. 154(b) by 308 days.

(21) Appl. No.: 09/901,910

(22) Filed: Jul. 11, 2001

(65) Prior Publication Data

US 2003/0012768 A1 Jan. 16, 2003

Related U.S. Application Data

(60) Provisional application No. 60/217,402, filed on Jul. 11, 2000, and provisional application No. 60/291,642, filed on May 18, 2001.

(51) Int. Cl.
- A61K 48/00 (2006.01)
- C12N 15/85 (2006.01)
- C12N 15/86 (2006.01)

(52) U.S. Cl. .......................... 514/44; 435/325
(58) Field of Classification Search .................. 514/2, 514/44; 435/325, 375, 6, 91.1
See application file for complete search history.

(56) References Cited

U.S. PATENT DOCUMENTS

| | | | |
|---|---|---|---|
| 5,408,040 | A | 4/1995 | Grotendorst et al. |
| 5,792,453 | A | 8/1998 | Hammond et al. |
| 5,837,258 | A | 11/1998 | Grotendorst |
| 5,944,710 | A | 8/1999 | Dev et al. |
| 6,051,424 | A | 4/2000 | Kato et al. |
| 6,069,006 | A | 5/2000 | Grotendorst et al. |

FOREIGN PATENT DOCUMENTS

| | | |
|---|---|---|
| EP | 0495674 | 7/1992 |
| WO | WO-88/03409 | 5/1988 |
| WO | WO-89/08667 | 9/1989 |
| WO | WO-94/03599 | 2/1994 |
| WO | WO 97/33995 | * 3/1997 |
| WO | WO-97/33995 | 9/1997 |
| WO | WO-00/35939 | 6/2000 |

OTHER PUBLICATIONS

Anderson, W.F. Human Gene Therapy. Nature, 1998 vol. 392(6679 Suppl):25–30.*
Anderson, W.F. The Current Status of Clinical Gene Therapy. Human Gene Therapy, 2002 vol. 13:1261–1262.*
Crystal, R. Transfer of Genes to HUmans: EArly Lessons and Obstacles to Success. Science, 1995 vol. 270:404–410.*
Brach, A. A Good Antisense Moleculer is Hard to Find. TIBS, Feb. 1998 vol. 23, pp. 45–50.*
Babic et al. CYR61, a product of a growth factor–inducible immediate early gene, promotes angiogenesis and tumor growth. Proc. Natl. Acad. Sci., 1998 vol. 95:6355–6360.*

(Continued)

Primary Examiner—Andrew Wang
Assistant Examiner—Terra C. Gibbs
(74) Attorney, Agent, or Firm—Human Genome Sciences, Inc.

(57) ABSTRACT

The present invention relates to a human CTGF-2 polypeptide and DNA (RNA) encoding such polypeptide. Also provided is a procedure for producing such polypeptide by recombinant techniques and antibodies and antagonist/inhibitors against such polypeptide. Also provided are methods of using the polypeptide therapeutically for stimulating angiogenesis enhancing the repair of connective and support tissue, promoting the attachment, fixation and stabilization of tissue implants and enhancing wound healing. Diagnostic assays for identifying mutations in nucleic acid sequence encoding a polypeptide of the present invention and for detecting altered levels of the polypeptide of the present invention are also disclosed.

11 Claims, 14 Drawing Sheets

OTHER PUBLICATIONS

Xie et al., "CRY61, an angiogenic inducer, is over-expressed and estrogen inducible in breast cancer." Proceedings of 91st Annual Meeting for Amer. Assoc. for Cancer Res., vol. 41 (Apr. 1, 2000).

Babic et al., "Fisp12/mouse connective tissue growth factor mediates endothelial cell adhesion and migration through integrin alphavabeta3, promotes endothelial cell survival, and induces angiogenesis in vivo." Mol Cell Biol. Apr. 1999;19(4):2958–66.

Jedsadayanmata et al., "Activation-dependent adhesion of human platelets to Cyr61 and Fisp12/mouse connective tissue growth factor is mediated through integrin alpha(llb-)beta(3)." J Biol Chem. Aug. 20, 1999;274(34):24321–7.

Shimo et al., "Inhibition of endogenous expression of connective tissue growth factor by its antisense oligonucleotide and antisense RNA suppresses proliferation and migration of vascular endothelial cells." J. Biochemistry v. 124(1) p. 130–140 (Jul. 1998).

Pakkanen et al., "Gene Therapy for Atherosclerosis and Atherosclerosis-Related Disease," *Current Atherosclerosis Rep.*, 1:123–130 (1999).

Diaz–Sandoval et al., "Gene therapy for cardiovascular angiogenesis," *Expert Opin. Biol. Ther.*, 3(4):599–616 (2003).

Nikol et al., "Vasular Gene Therapy—Preclinical and Clinical Experience in Vascular Gene Therapy: Advantages Over Conservative/Standard Therapy," *J. Invas. Cardiol.*, 13:333–338 (2001).

Geneseq Accession No. AAT97142, Toyobo, K.K., "Human monocyte mature differentiation factor encoding cDNA" (Mar. 5, 1998).

Geneseq Accession No. AAW35957, Toyobo, K.K., "A monocyte mature differentiation factor—useful for the long term tissue culture of macrophage(s)" (Mar. 5, 1998).

Geneseq Accession No. AAT94699, Lau, L.F., "Human cysteine rich protein 61 (Cyr61) cDNA" (Mar. 27, 1998).

Geneseq Accession No. AAW35730, Lau, L.F., "Human cysteine rich protein 61 (Cyr61)" (Mar. 27, 1998).

International Search Report for PCT/US01/21799.

Latinkic et al., "Promoter function and structure of the growth factor-inducible immediate early gene cyr61," *Nucleic Acids Research*, 19(12):3261–3267 (1991).

O'Brien et al., "Expression of cry61, a Growth Factor-Inducible Immediate–Early Gene," *Molec. and Cell. Biol.*, 10(7):3569–3577 (Jul. 1990).

Simmons et al.,"Identification of a phorbol ester-repressible v-src-inducible gene." *PNAS*, USA, 86:1178–1182 (1989).

Oemar et al., "Molecular cloning and expression of human connective tissue growth factor," *Hypertension*, 22(3):424 (1993).

Oemar et al.,"Expression of recombinant human connective tissue growth factor in insect cells," *European Heart Journal*, 15(Abstr. Suppl.):486 (1994).

Bradham et al.,"Connective tissue growth factor: a cysteine-rich mitogen secreted by human vascular endothelial cells is related to the SRC-induced immediate early gene product CEF–10," *J. Cell Biol.*, 114(6):1285–1294 (1991).

George et al., "Current methods in sequence comparison and analysis," in *Macromolecular Sequencing and Synthesis, Selected Methods and Applications*, D.H. Schlesinger (ed.), Alan R. Liss, Inc., New York, NY, pp. 127–149 (1988).

Boswell et al., "Sequence Comparison and alignemnt: the measurement and interpretation of sequence similarity," in *Computational Molecular Biology: Sources and Methods for Sequence Analysis*, Arthur M. Lesk (ed.), Oxford University Press, New York, NY, pp. 161–178 (1988).

O'Brien et al., "Expression of the growth factor-inducible immediate early gene cyr61 correlates with chondrogenesis during mouse embryonic development," in *Cell Growth Differe.*, 3(9):6645–654 (Sep. 1992).

GeneSeq Accession No. Q26421, Brunner, A.M., "TGF-beta induced gene family—encodes proteins involved in growth and differentitation effects of TGF–beta–1" (Jan. 18, 1993).

GeneSeq Accession No. Q26422, Brunner, A.M., "TGF-beta induced gene family—encodes proteins involved in growth and differentiation effects of TGF–beta–1" (Jan. 18, 1993).

GeneSeq Accession No. R25565, Brunner, A.M., "TGF-beta induced gene family—encodes proteins involved in growth and differentiation effects of TGF–beta–1" (Jan. 18, 1993).

GeneSeq Accession No. R25566, Brunner, A.M., "TGF-beta induced gene family—encodes proteins involved in growth and differentiation effects of TGF–beta–1" (Jan. 18, 1993).

GeneSeq Accession No. R46078, Iwahori, A., "cDNA of human origin and proteins coded by it—which may be expressed by in vivo or in vitro translation using sense RNA or antisense DNA corresponding to the cDNA" (Oct. 19, 1994).

GeneSeq Accession No. Q57417, Iwahori, A., "cDNA of human origin and proteins coded by it—which may be expressed by in vivo or in vitro translation using sense RNA or antisense DNA corresponding to the cDNA" (Jan. 19, 1994).

* cited by examiner

Figure 1A

| | | |
|---|---|---|
| 1 | ATGAGCTCCCGCATCGCCAGGGCGCTCGCCTTAGTCGTCACCCTTCTCCACTTGACCAGG | 60 |
| 1 | M  S  S  R  I  A  R  A  L  A  L  V  V  T  L  L  H  L  T  R | 20 |
| 61 | CTGGCGCTCTCCACCTGCCCCGCTGCCTGCCACTGCCCCCTGGAGGCGCCCAAGTGCGCG | 120 |
| 21 | L  A  L  S  T  C  P  A  A  C  H  C  P  L  E  A  P  K  C  A | 40 |
| 121 | CCGGGAGTCGGGCTGGTCCGGGACGGCTGCGGCTGCTGTAAGGTCTGCGCCAAGCAGCTC | 180 |
| 41 | P  G  V  G  L  V  R  D  G  C  G  C  C  K  V  C  A  K  Q  L | 60 |
| 181 | AACGAGGACTGCAGCAAAACGCAGCCCTGCGACCACACCAAGGGGCTGGAATGCAACTTC | 240 |
| 61 | N  E  D  C  S  K  T  Q  P  C  D  H  T  K  G  L  E  C  N  F | 80 |
| 241 | GGCGCCAGCTCCACCGCTCTGAAGGGGATCTGCAGAGCTCAGTCAGAGGGCAGACCCTGT | 300 |
| 81 | G  A  S  S  T  A  L  K  G  I  C  R  A  Q  S  E  G  R  P  C | 100 |
| 301 | GAATATAACTCCAGAATCTACCAAAACGGGGAAAGTTTCCAGCCCAACTGTAAACATCAG | 360 |
| 101 | E  Y  N  S  R  I  Y  Q  N  G  E  S  F  Q  P  N  C  K  H  Q | 120 |
| 361 | TGCACATGTATTGATGGCGCCGTGGGCTGCATTCCTCTGTGTCCCCAAGAACTATCTCTC | 420 |
| 121 | C  T  C  I  D  G  A  V  G  C  I  P  L  C  P  Q  E  L  S  L | 140 |
| 421 | CCCAACTTGGGCTGTCCCAACCCTCGGCTGGTCAAAGTTACCGGGCAGTGCTGCGAGGAG | 480 |
| 141 | P  N  L  G  C  P  N  P  R  L  V  K  V  T  G  Q  C  C  E  E | 160 |
| 481 | TGGGTCTGTGACGAGGATAGTATCAAGGACCCCATGGAGGACCAGGACGGCCTCCTTGGC | 540 |
| 161 | W  V  C  D  E  D  S  I  K  D  P  M  E  D  Q  D  G  L  L  G | 180 |
| 541 | AAGGAGCTGGGATTCGATGCCTCCGAGGTGGAGTTGACGAGAAACAATGAATTGATTGCA | 600 |
| 181 | K  E  L  G  F  D  A  S  E  V  E  L  T  R  N  N  E  L  I  A | 200 |
| 601 | GTTGGAAAAGGCAGCTCACTGAAGCGGCTCCCTGTTTTTGGAATGGAGCCTCGCATCCTA | 660 |
| 201 | V  G  K  G  S  S  L  K  R  L  P  V  F  G  M  E  P  R  I  L | 220 |
| 661 | TACAACCCTTTACAAGGCCAGAAATGTATTGTTCAAACAACTTCATGGTCCCAGTGCTCA | 720 |
| 221 | Y  N  P  L  Q  G  Q  K  C  I  V  Q  T  T  S  W  S  Q  C  S | 240 |
| 721 | AAGACCTGTGGAACTGGTATCTCCACACGAGTTACCAATGACAACCCTGAGTGCCGCCTT | 780 |
| 241 | K  T  C  G  T  G  I  S  T  R  V  T  N  D  N  P  E  C  R  L | 260 |
| 781 | GTGAAAGAAACCCGGATTTGTGAGGTGCGGCCTTGTGGACAGCCAGTGTACAGCAGCCTG | 840 |
| 261 | V  K  E  T  R  I  C  E  V  R  P  C  G  Q  P  V  Y  S  S  L | 280 |

Figure 1B

```
 841  AAAAAGGGCAAGAAATGCAGCAAGACCAAGAAATCCCCCGAACCAGTCAGGTTTACTTAC   900
 281   K  K  G  K  K  C  S  K  T  K  K  S  P  E  P  V  R  F  T  Y    300

901  GCTGGATGTTTGAGTGTGAAGAAATACCGGCCCAAGTACTGCGGTTCCTGCGTGGACGGC   960
 301   A  G  C  L  S  V  K  K  Y  R  P  K  Y  C  G  S  C  V  D  G    320

961  CGATGCTGCACGCCCCAGCTGACCAGGACTGTGAAGATGCGGTTCCGCTGCGAAGATGGG  1020
 321   R  C  C  T  P  Q  L  T  R  T  V  K  M  R  F  R  C  E  D  G    340

1021  GAGACATTTTCCAAGAACGTCATGATGATCCAGTCCTGCAAATGCAACTACAACTGCCCG  1080
 341   E  T  F  S  K  N  V  M  M  I  Q  S  C  K  C  N  Y  N  C  P    360

1081  CATGCCAATGAAGCAGCGTTTCCCTTCTACAGGCTGTTCAATGACATTCACAAATTTAGG  1140
 361   H  A  N  E  A  A  F  P  F  Y  R  L  F  N  D  I  H  K  F  R    380

1141  GACTAA                                                        1146
 381   D  *                                                          382
```

Figure 11A

```
ATGAGCTCCCGAATCGTCAGGGAGCTCGCCTTAGTCGTCACCCTTCTCCACTTGACCAGG
 M  S  S  R  I  V  R  E  L  A  L  V  V  T  L  L  H  L  T  R

GTGGGGCTCTCCACCTGCCCCCCGCTGACTGCCACTGCCCCCTGGAGGCGCCAAGTGCGCG
 V  G  L  S  T  C  P  A  D  C  H  C  P  L  E  A  P  K  C  A

CCGGGAGTCGGGCTGGTCCGGGACGGCTGCGGCTGTGTTGTAAGGTCTGCGCCAAGCAGCTC
 P  G  V  G  L  V  R  D  G  C  G  C  V  C  A  K  Q  L

AACGAGGACTGCAGAAAAACGCAGCCCTGCCGACCACACCAAGGGCTGGAATGCAACTTC
 N  E  D  C  R  K  T  Q  P  C  D  H  T  K  G  L  E  C  N  F

GGCGCCAGTCCACCGGCTCTGAAGGGGATCTGCAGAGCTCAGTCAGAGGGCAGACCCTGT
 G  A  S  S  T  A  L  K  G  I  C  R  A  Q  S  E  G  R  P  C

GAATATAACTCCAGAATCTACCAAAACGGGGAAAGTTTCCAGCCCAACTGTAAACATCAG
 E  Y  N  S  R  I  Y  Q  N  G  E  S  F  Q  P  N  C  K  H  Q

TGCACAATGTATTGGATGGCCCCGGGGCTTGCATTCCTCTGTGTCCCCAAGAACTATCT
 C  T  C  I  G  W  R  R  G  A  C  I  P  L  C  P  Q  E  L  S
```

```
CTCCCCAACTTGGGCTGTCCCAACCCTCGGCTGGTCAAAGTTACCGGGCAGTGCTGCGAG
 L  P  N  L  G  C  P  N  P  R  L  V  K  V  T  G  Q  C  C  E

GAGTGGGTCTGTGACGAGGATAGTATCAAGGACCCCATGGAGGACCAGGACGGCCTCCTT
 E  W  V  C  D  E  D  S  I  K  D  P  M  E  D  Q  D  G  L  L

GGCAAGGGGCTGGACTTCGATGCCTCCGAGGTTGAGTTGACGAGAAACAATGAATTGATT
 G  K  G  L  G  F  D  A  S  E  V  E  L  T  R  N  N  E  L  I

GCAGTTGGAAAAGGCAGCTCACTGAAGCGGCTCCCTGTTTTTGGAATGGAGCCTCGCATC
 A  V  G  K  G  S  S  L  K  R  L  P  V  F  G  M  E  P  R  I

CTATACAACCCTTTACAAGGCCAGAAATGTATTCTTCAAACAACTTCATGGTCCCAGTGC
 L  Y  N  P  L  Q  G  Q  K  C  I  V  Q  T  T  S  W  S  Q  C

TCAAAGACCTGTGAACTGGTATCTCCACACGAGTTACCAATGACAACCCTGAGTGCCGC
 S  K  T  C  G  T  G  I  S  T  R  V  T  N  D  N  P  E  C  R

CTTGTGAAAGAAACCCGGATTTGTGAGGTGCGCCTTGTGGACAGCCAGTGTACAGCAGC
 L  V  K  E  T  R  I  C  E  V  R  P  C  G  Q  P  V  Y  S  S
```

Figure 11C

```
CTGAAAAAGGGCAAGAAAATGCAGCAAGACCAAGAATCCCCGAACCAGTCAGGTTTACT
 L  K  K  G  K  K  C  S  K  T  K  K  S  P  E  P  V  R  F  T

TACGCTGGATGTGTTTGAGTGTGTGAAGAAATACCGGCCCAAGTACTGCGGTTCCTGCGTGGAC
 Y  A  G  C  L  S  V  K  K  Y  R  P  K  Y  C  G  S  C  V  D

GGCCGATGCTGCACGCCCCAGCTGACCAGGACTGTGAAGATGCGGTTCCCTGCGAAGAT
 G  R  C  C  T  P  Q  L  T  R  T  V  K  M  R  F  P  C  E  D

GGGGAGACATTTTCCAAGAACGTCATGATGATCCAGTCCTCCAAATGCAACTACAACTGC
 G  E  T  F  S  K  N  V  M  M  I  Q  S  S  K  C  N  Y  N  C

CCGCATGCCAATGAAGCAGCCGTTTCCCTTCTACAGGCTGTTCCAATGA
 P  H  A  N  E  A  A  F  P  F  Y  R  L  F  Q  .
```

CONNECTIVE TISSUE GROWTH FACTOR-2

This application claims benefit under 35 U.S.C. § 119(e) of U.S. Provisional Application Nos. 60/217,402, filed Jul. 11, 2000 and 60/291,642 filed May 18, 2001, each of which is hereby incorporated by reference in its entirety. U.S. patent application Ser. No. 09/348,815, filed Jul. 8, 1999, U.S. patent application Ser. No. 08/459,101, filed Jun. 2, 1995, and International Application No. PCT/US94/07736, filed Jul. 12, 1994, are also hereby incorporated by reference in their entirety.

INTRODUCTION

This invention relates to newly identified polynucleotides, polypeptides encoded by such polynucleotides, the use of such polynucleotides and polypeptides, as well as the production of such polynucleotides and polypeptides. More particularly, the polypeptide of the present invention is connective tissue growth factor-2 sometimes hereinafter referred to as "CTGF-2". The invention also relates to inhibiting the action of such polypeptides. In addition, the invention encompasses methods of using CTGF-2 polynucleotides and polypeptides to stimulate angiogenesis, i.e., formation of new blood vessels. The invention also encompasses methods of treatment of atherosclerosis, ischemia, restenosis.

BACKGROUND OF THE INVENTION

The CTGF polypeptides are structurally and functionally related to a family of growth factors which include IGF (insulin-like growth factor), PDGF (platelet-derived growth factor), and FGF (fibroblast growth factor). This emerging family of secreted proteins are a group of cysteine-rich proteins. This group of growth factors are important for normal growth, differentiation, morphogenesis of the cartilaginous skeleton of an embryo and cell growth. Among some of the functions that have been discovered for these growth factors are wound healing, tissue repair, implant fixation and stimulating increased bone mass.

The extended superfamily of growth factors include TGF (transforming growth factor), bone morphogenic factors, and activins, among others.

The most well-known growth factor, TGF exerts a number of different effects on a variety of cells. For example, TGF-alpha can inhibit the differentiation of certain cells of mesodermal origin (Florini, J. R. et al., *J. Biol. Chem.*, 261:1659–16513 (1986) induced the differentiation of others (Seyedine, S. M. et al., *PNAS USA*, 82:2267–2271 (1987) and potently inhibit proliferation of various types of epithelial cells, (Tucker, R. F., *Science*, 226:705–705 (1984)). This last activity has led to the speculation that one important physiological role for TGF-" is to maintain the repressed growth state of many types of cells. Accordingly, cells that lose the ability to respond to TGF-" are more likely to exhibit uncontrolled growth and become tumorigenic.

Accordingly, due to amino acid sequence homology the polypeptide of the present invention is a member of this extended family of growth factors which has many effects on a variety of different tissues.

SUMMARY OF THE INVENTION

In accordance with one aspect of the present invention, there is provided a novel CTGF-2 polypeptide, as well as biologically active and diagnostically or therapeutically useful fragments, analogs and derivatives thereof. The polypeptide of the present invention is of human origin.

In accordance with another aspect of the present invention, there are provided isolated nucleic acid molecules encoding such CTGF-2 polypeptide and polypeptide fragments, analogs, and derivatives of the present invention, including mRNAs, DNAs, cDNAs, genomic DNAs as well as analogs and biologically active and diagnostically or therapeutically useful fragments thereof.

In accordance with yet a further aspect of the present invention, there is provided a process for producing such polypeptide by recombinant techniques comprising culturing recombinant prokaryotic and/or eukaryotic host cells, containing a nucleic acid sequence encoding a polypeptide of the present invention, under conditions promoting expression of said protein and subsequent recovery of said protein.

In accordance with yet a further aspect of the present invention, there is provided a process for utilizing such polypeptide, or polynucleotide encoding such polypeptide for therapeutic purposes, for example, enhancing the repair of connective and support tissue, promoting the attachment, fixation and stabilization of tissue implants and enhancing wound healing. In addition methods for stimulating angiogenesis, i.e., formation of new blood vessels, using the polynucleotides and polypeptides of the invention are provided. Such methods include, but are not limited to, gene therapy of patients in need of new blood vessel formation. Thus, the polynucleotides and polypeptides of the invention are useful in the treatment of cardiovascular disease, including but not limited to atherosclerosis, restenosis, reperfusion injury Such disorders include, but are not limited to, heart failure, angina, blood vessel (e.g. coronary artery) blockage and ischemia, inlcuding critical limb ischemia and refractory myocardial ischemia.

In accordance with yet a further aspect of the invention, vectors are provided for use in administering the polynucleotides of the invention.

In accordance with yet a further aspect of the present invention, there are provided antibodies against such polypeptides.

In accordance with yet a further aspect of the present invention, there is also provided nucleic acid probes comprising nucleic acid molecules of sufficient length to specifically hybridize to a nucleic acid sequence of the present invention.

In accordance with yet a further aspect of the present invention, there are provided antibodies against such polypeptides.

In accordance with another aspect of the present invention, there are provided agonists which mimic the polypeptide of the present invention and binds to the receptors.

In accordance with yet another aspect of the present invention, there are provided antagonists to such polypeptides, which may be used to inhibit the action of such polypeptides, for example, in the treatment of CTGF dependent tumor growth.

In accordance with still another aspect of the present invention, there are provided diagnostic assays for detecting diseases or susceptibility to diseases related to mutations in the nucleic acid sequences encoding a polypeptide of the present invention.

In accordance with yet a further aspect of the present invention, there is provided a process for utilizing such polypeptides, or polynucleotides encoding such polypeptides, for in vitro purposes related to scientific research, for example, synthesis of DNA and manufacture of DNA vectors.

These and other aspects of the present invention should be apparent to those skilled in the art from the teachings herein.

The following drawings are illustrative of embodiments of the invention and are not meant to limit the scope of the invention as encompassed by the claims.

BRIEF DESCRIPTION OF THE FIGURES

FIGS. 1A–B: FIGS. 1A–B depict the cDNA sequence (SEQ ID NO:1) and corresponding deduced amino acid sequence (SEQ ID NO:2) of CTGF-2. The standard one-letter abbreviation for amino acids is used.

*$P<0.05$ vs Ad-Null; Non significant (NS) vs Ad-VEGF$_{165}$

Figure 3:
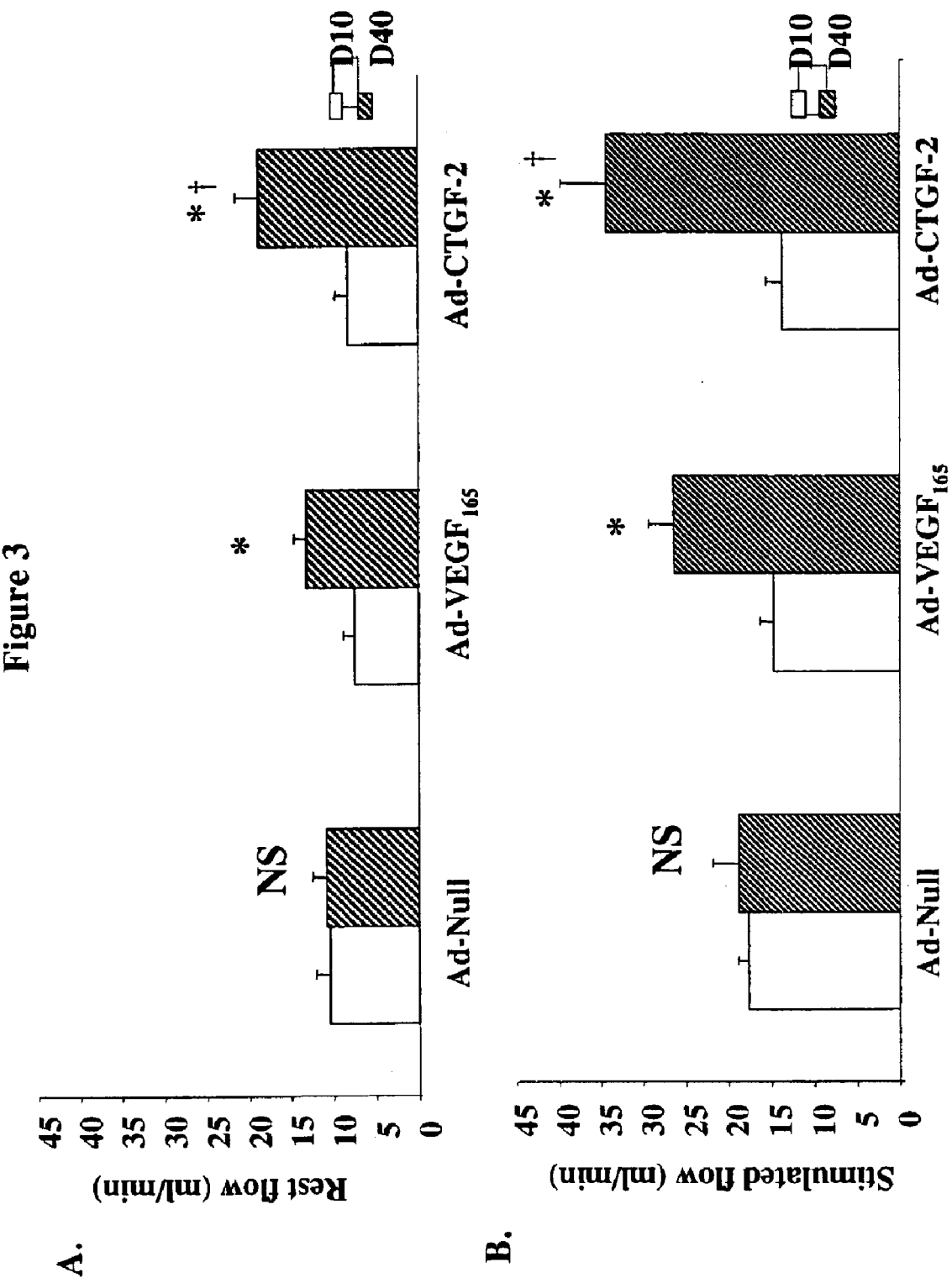

FIG. 3: Calculated blood flow at rest (A) and after papaverine injection (B) in the ischemic limb. Ad-VEGF$_{165}$ and Ad-CTGF-2-treated animals had a significant increase in flows when day 40 is compared with day 10 both at rest and after papaverine infusion. At day 40, rest flow as well as maximum flow were significantly improved in Ad-CTGF-2 animals compared with Ad-Null group. Although a trend toward greater blood flows improvement appeared in Ad-CTGF-2 in comparison with Ad-VEGF$_{165}$-treated rabbits, there was no statistical difference between these two groups.

Figure 4:
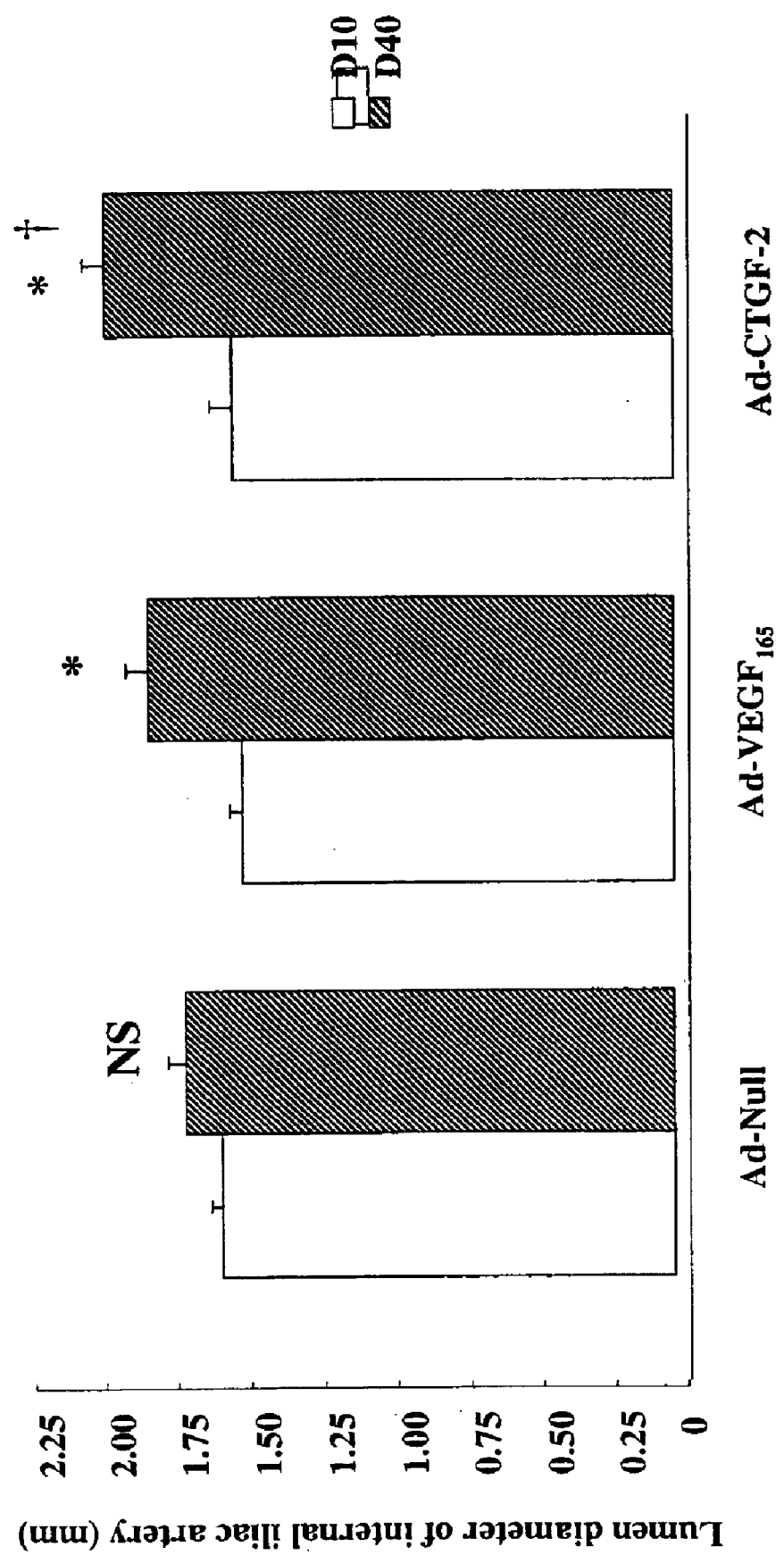

NS vs day 10 in the same group
*$P<0.01$ vs day 10 in the same group
?$P<0.05$ vs Ad-Null-treated rabbits FIG. 4: Serial assessement of internal iliac artery luminal diameter in the ischemic limb.

During the 30 days of the follow-up period, a significant increase in angiographic luminal diameter was recorded only for Ad-VEGF$_{165}$ and Ad-CTGF-2-treated animals. At day 40, mean diameter of the Ad-CTGF-2 group appeared higher compared to the Ad-Null group.

*$P<0.001$ vs day 10 in the same group
?$P<0.05$ vs Ad-Null-treated rabbits

Figure 5:
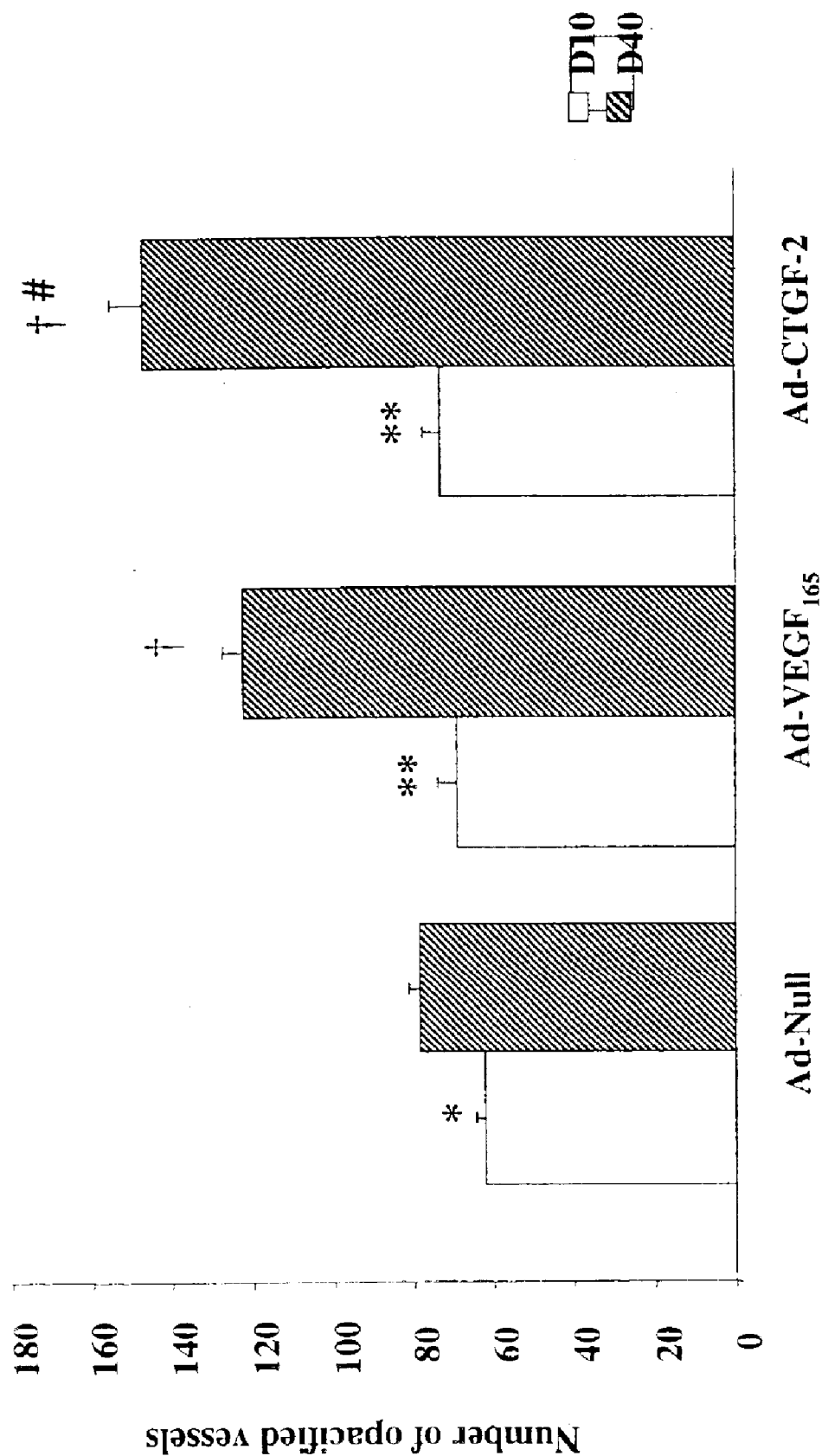

FIG. 5: Representative angiograms of the ischemic limb recorded on day 10 (upper views) and on day 40 (lower views) from A) Ad-Null, B) Ad-VEGF$_{165}$ and C) Ad-CTGF-2-treated animals showing collateral vessel formation through the 30 days follow-up period. The morphology of the augmented collateral circulation was typically made of fine networks of so-called midzone collateral vessels. In some cases, serial angiograms disclosed progressive linear extension of the stem artery to the reentry (popliteal or saphenous arteries), predominantly for Ad-CTGF-2-treated rabbits.

Figure 6:
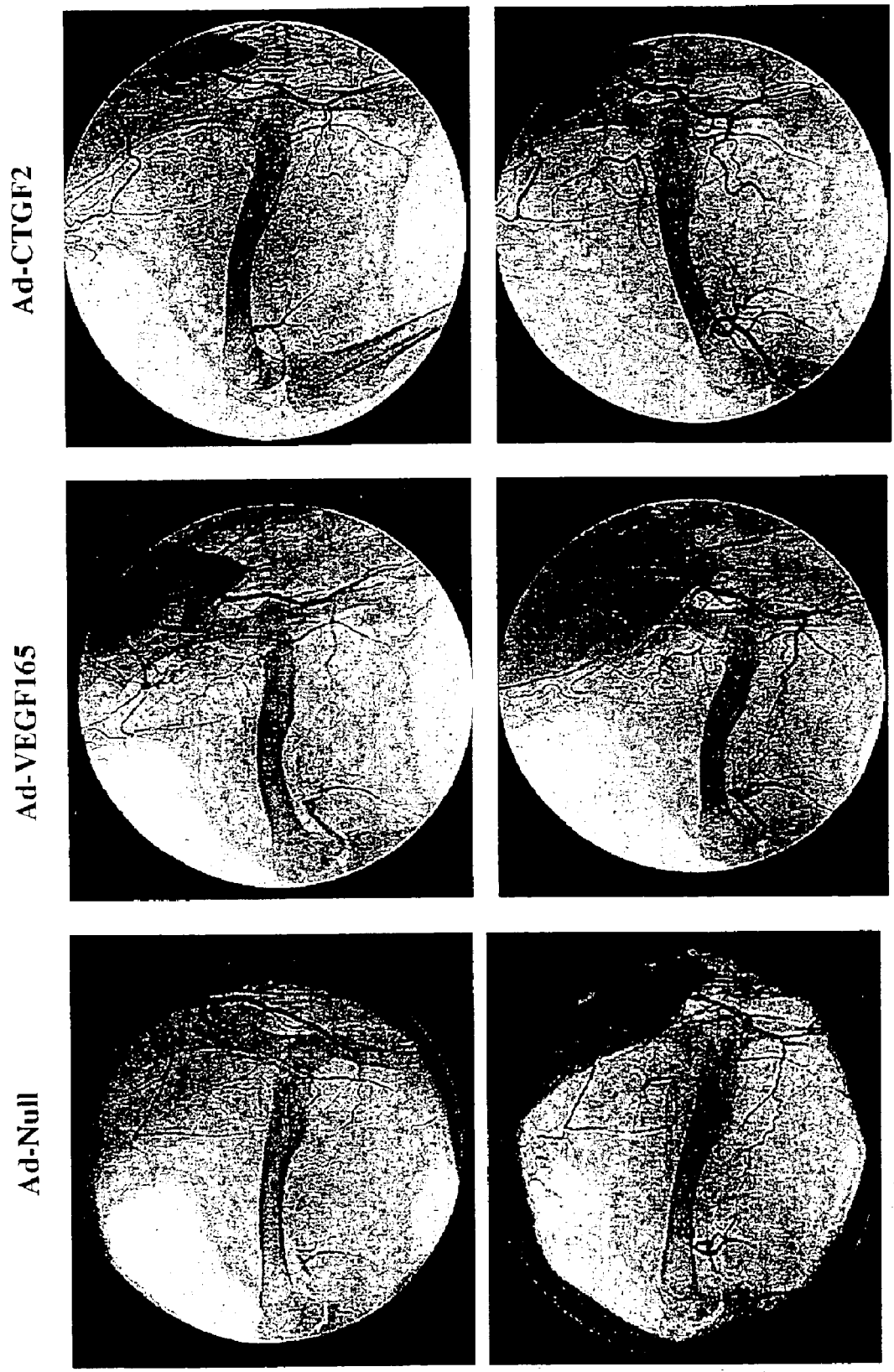

FIG. 6: Quantitative angiographic analysis of collateral vessel development in the medial thigh of ischemic hindlimb evaluated by an angiographic score. The vascular density was significantly improved for each group at day 40 compared to day 10. Angiographic scores at day 40 were significantly higher in both treated groups compared to control animals and, in CTGF-2-treated animals it exceeded that of the VEGF$_{165}$-treated group.

Figure 7:
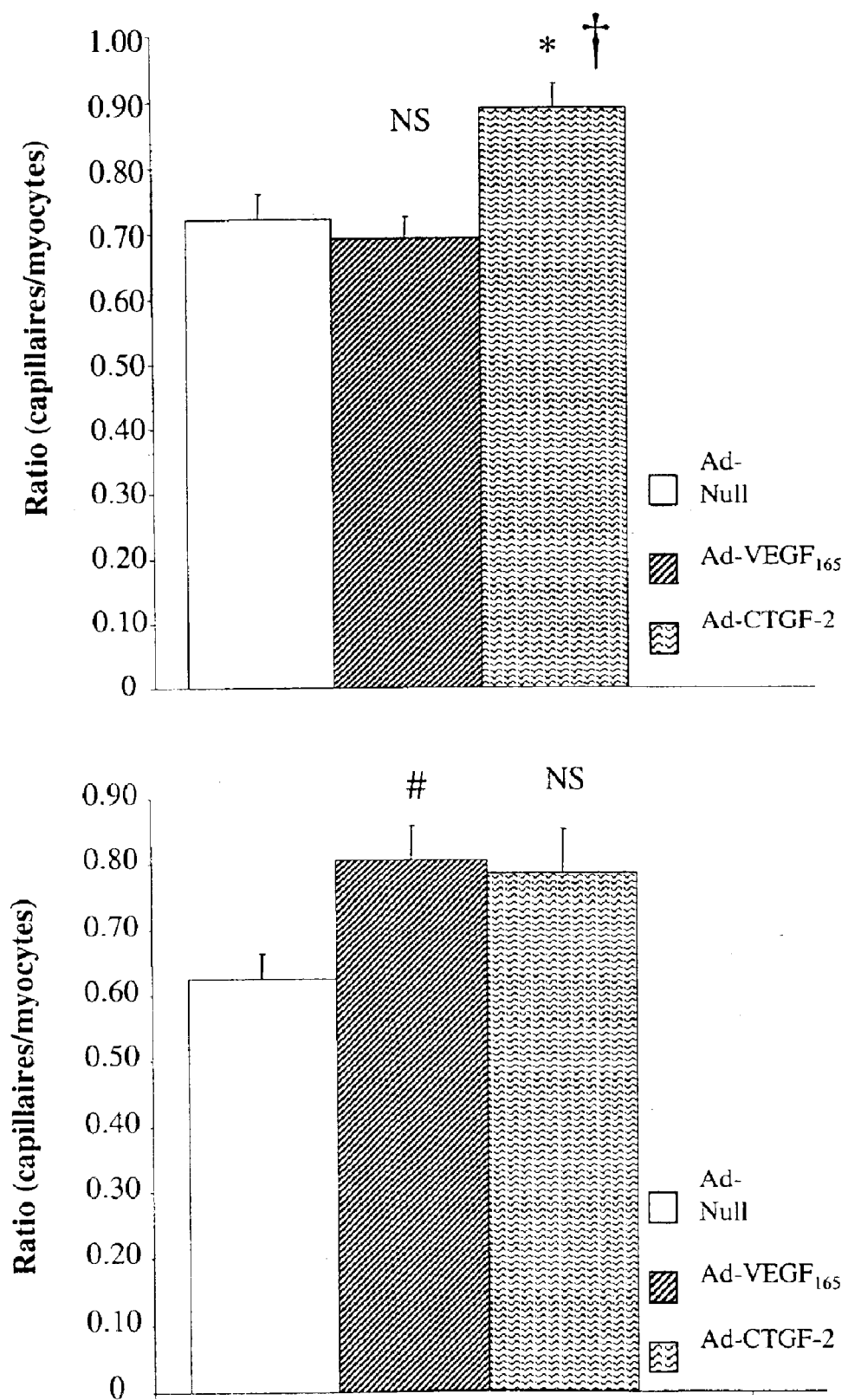

*$P<0.01$ vs day 40 in the same group
**$P<0.001$ vs day 40 in the same group
?$P<0.0001$ vs Ad-Null-treated rabbits
$P<0.01$ vs Ad-VEGF$_{165}$-treated rabbits FIG. 7: Capillary density evaluated on histological sections of adductor (A) and (B) semimembranous muscles harvested at the time of sacrifice (day 40). In the adductor muscle, the capillary-to-myocyte ratio was statistically increased in the Ad-CTGF-2 group compared with the Ad-Null and Ad-VEGF$_{165}$-treated animals. In the semimembranous muscle, the ratio was increased for the Ad-VEGF$_{165}$ compared to the Ad-Null whereas the increase seen for Ad-CTGF-2 did not attain the level of significance.

Figure 8:
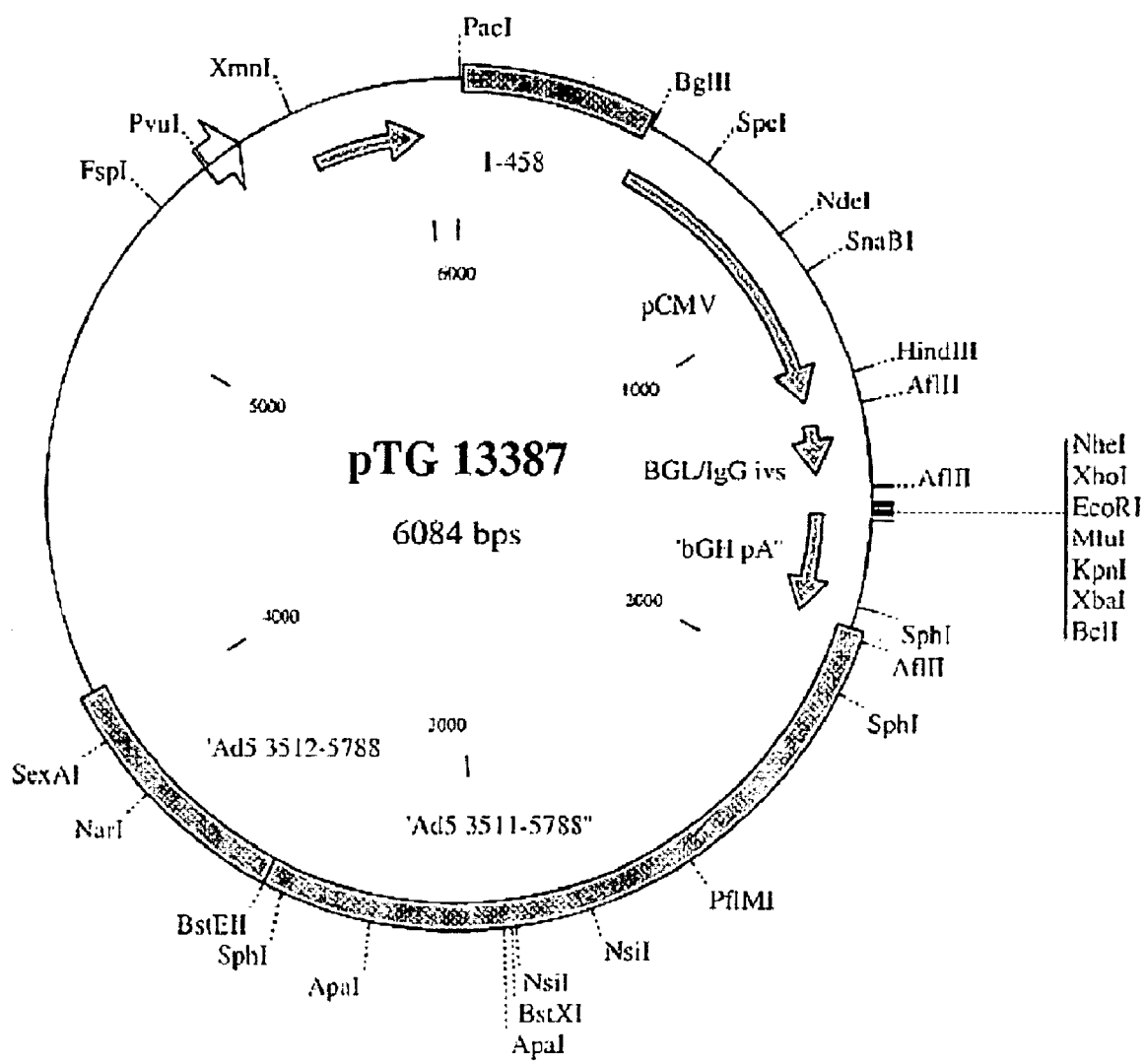

NS vs Ad-Null-treated rabbits
*$P<0.01$ vs Ad-Null-treated rabbits
?$P<0.001$ vs Ad-VEGF$_{165}$-treated rabbits
$P<0.05$ vs Ad-Null-treated rabbits FIG. 8: FIG. 8 shows the vector map of the transfer vector pTG13387. This transfer vector contains the Ad5 1–458 region followed by the CMV enhancer/promoter and a chimeric intron generated by combining the splice donor from the human β-globin intron 1 and the splice acceptor from the IgG intervening sequence obtained from pCI plasmid (Promega, Charbonnieres, France).

Figure 9:
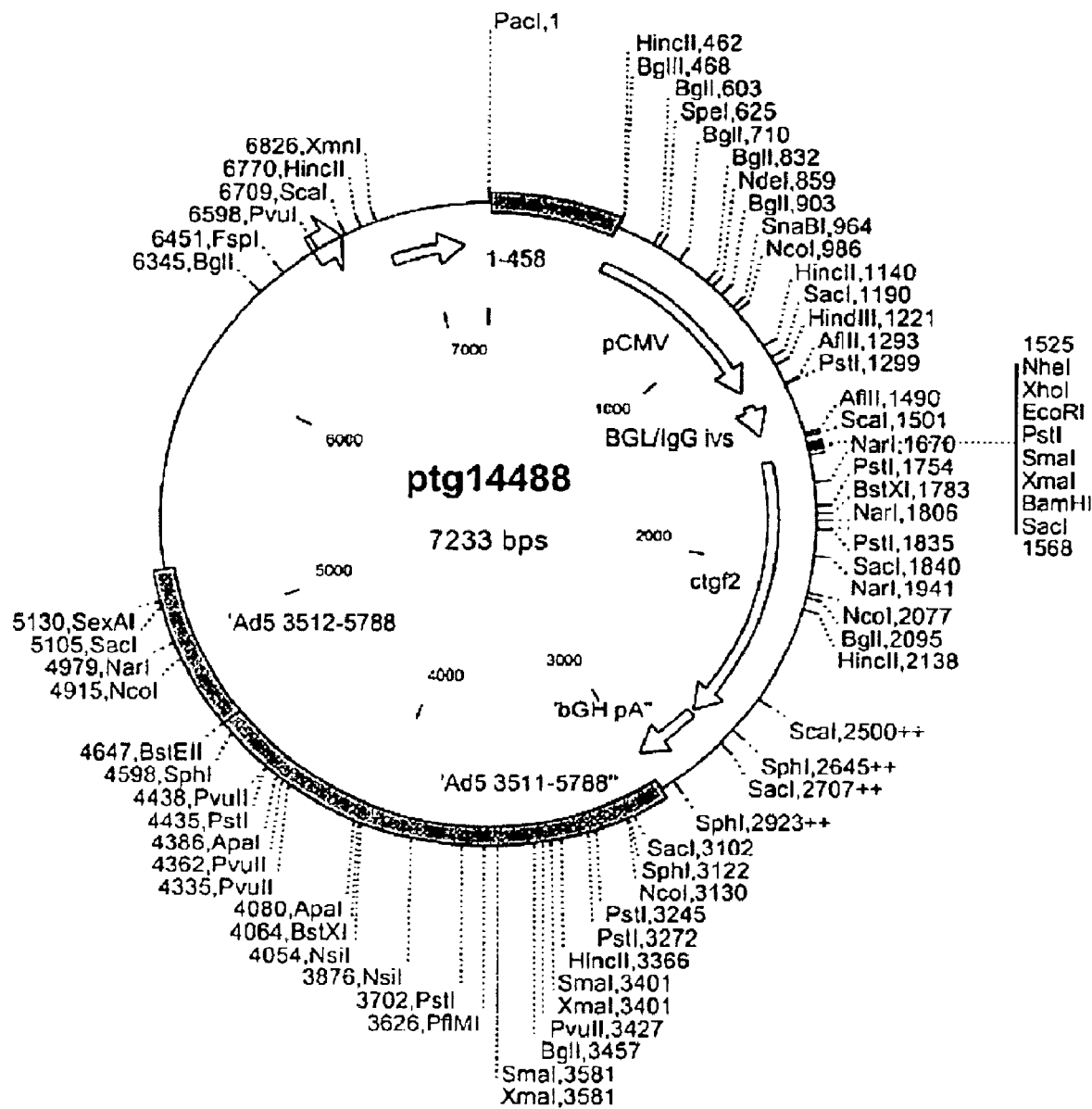

FIG. 9: FIG. 9 shows the vector map of the CTGF-2 transfer vector ptg14488.

Figure 10:
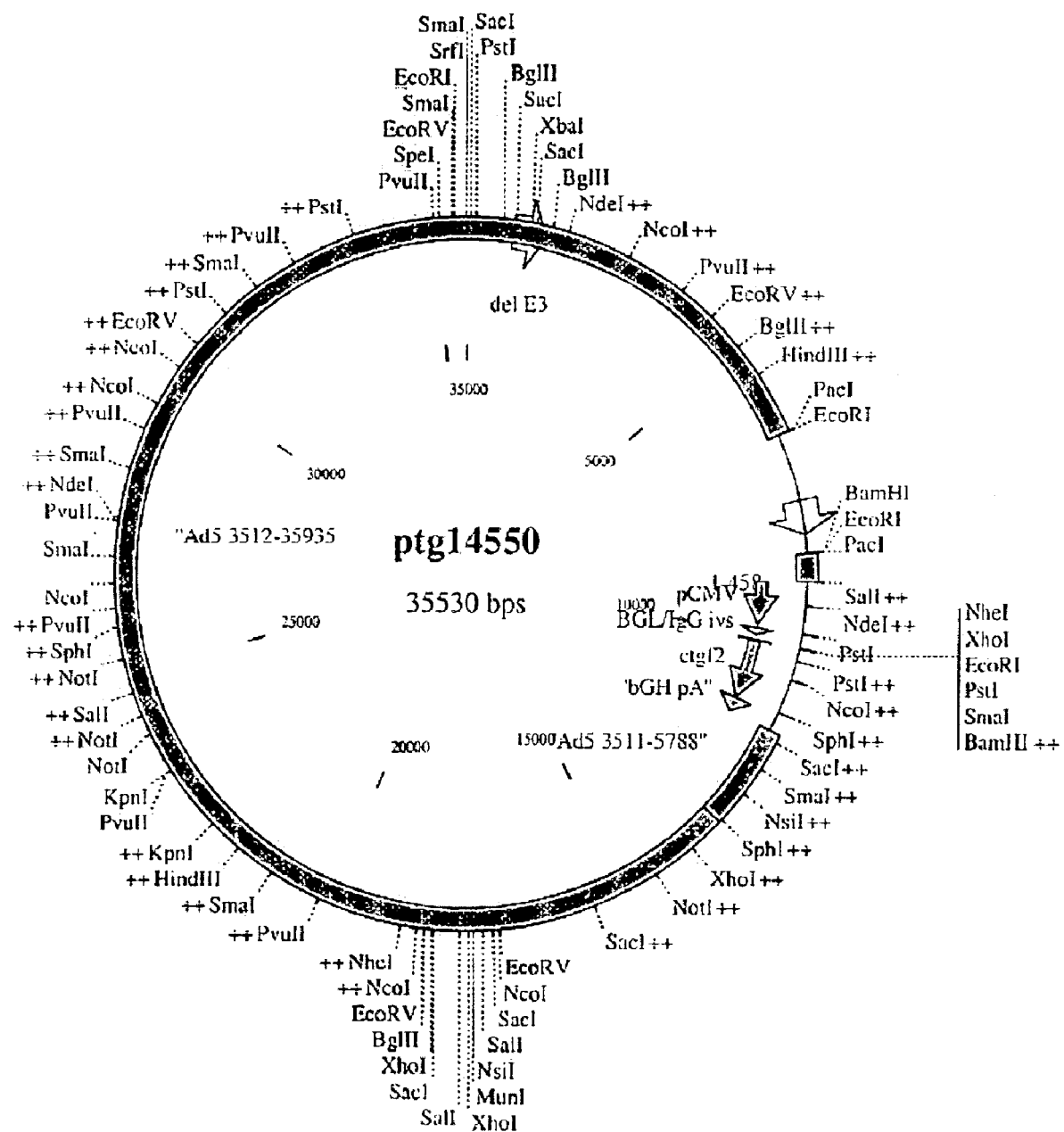

FIG. 10: FIG. 10 shows the vector map of the adenoviral vector ptg14550.

FIGS. 11A–C: FIG. 11 depicts an idternazive cDNA sequence (SEQ ID NO:6) and corresponding deduced amino acid sequence (SEQ ID NO:7) of CTGF-2. The srandard one-letter abbreviation far amino acids is used.

DETAILED DESCRIPTION OF THE INVENTION

In accordance with an aspect of the present invention, there is provided an isolated nucleic acid (polynucleotide) (SEQ ID NO:1) which encodes for the polypeptide having the deduced amino acid sequence of FIGS. 1A–B (SEQ ID NO:2) or as encoded by the cDNA of the clone deposited as with the American Type Culture Collection (ATCC) on Jun. 7, 1994 as Deposit No. 75804. An alternative cDNA sequence (SEQ ID NO:6) and corresponding deduced amino acid sequence (SEQ ID NO:7) of CTGF-2 is demonstrated in FIGS. 11A–C.

In accordance with an additional aspect of the present invention, there is provided a nucleic acid vector for gene therapy-based methods of delivering polynucleotides encoding the CTGF-2 polypeptide having the amino acid sequence of FIGS. 1A–B as described in Example 12, which was deposited with the Pasteur Institute Depository on Jul. 9, 2001, having received the registration number CNCM I-2695. The Pasteur Institute Depository is located at the following address: Collection Nationale de Cultures de Microorganismes, INSTITUT PASTEUR, 25, rue du DOCTEUR ROUX, F-74724 Paris Cedex 15, France.

The polynucleotide of this invention was discovered in a cDNA library derived from human fetal lung. It is structurally related to the IGF and PDGF family. It contains an open reading frame encoding a protein of 382 amino acid residues of which approximately the first 23 or 24 amino acids residues are the putative leader sequence such that the putative mature protein comprises 358 amino acids (residues 24–382 or 25–382). In addition to the leader sequence, CTGF-2 contains an IGF Binding Domain that extends from about amino acid Ser-24 to about Ala-93; a von Willebrand Factor Type C Repeat Domain from about amino acid Arg-98 to about amino acid Asp-164; a Sulfated Glycoconjugate Binding Motif from about amino acid Cys-229 to about amino acid Gly-273; and a C-Terminal Dimerization and Receptor Binding Domain from about amino acid Cys-286 to about amino acid His-361. In this context "about" includes the particularly recited ranges, larger or smaller by several (5, 4, 3, 2, or 1) nucleotides, at either terminus or at both termini.

The protein exhibits a high degree of homology to Mouse CTGF with 49% identity and 67% similarity and to Cyr61 with 89% identity and 93% similarity. Cyr61 is a growth factor-inducible immediate early gene initially identified in serum-stimulated mouse fibroblasts. It encodes a member of an emerging family of cysteine-rich secreted proteins that includes a connective tissue growth factor (O'Brien and Lau, L. F., Cell Growth Differ., 3:645–54 (1992)).

In accordance with the invention, CTGF-2 is active in stimulating angiogenesis. Thus, novel methods for stimulating angiogenesis, i.e., formation of new blood vessels, using the polynucleotides and polypeptides of the invention are provided. Such methods include, but are not limited to, gene therapy of patients in need of new blood vessel formation. Thus, the polynucleotides and polypeptides of the invention are useful in the treatment of cardiovascular disease, including but not limited to atherosclerosis, restenosis, reperfusion injury Such disorders include, but are not limited to, heart failure, angina, blood vessel (e.g. coronary artery) blockage and ischemia, including critical limb ischemia and refractory myocardial ischemia.

Nucleic Acid Embodiments

The CTGF-2 polynucleotides and derivatives described herein below are useful, for example, in the production of CTGF-2 polypeptide and polypeptide derivatives (described below), as well as as agents in gene therapy to stimulate angiogenesis, as described in detail below. The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–B or that of the deposited clone in ATCC accession no. 75804, or may be a different coding sequence which coding sequence, as a result of the redundancy or degeneracy of the genetic code, encodes the same mature polypeptide as the DNA of FIGS. 1A–B or the deposited cDNA.

The polynucleotide which encodes for the mature polypeptide of FIGS. 1A–B or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A–B or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A–B or the same mature polypeptide encoded by the cDNA of the deposited clone as well as variants of such polynucleotides which variants encode for a fragment, derivative or analog of the polypeptide of FIGS. 1A–B or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–B or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promoter regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 90%, and more preferably at least 95% identity between the sequences. The present invention particularly relates to polynucleotides which hybridize under stringent conditions to the hereinabove-described polynucleotides. The polynucleotides which hybridize to the hereinabove described polynucleotides in a preferred embodiment encode polypeptides which either retain substantially the same biological function or activity as the mature polypeptide encoded by the cDNAs of FIGS. 1A–B or the deposited cDNA.

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of FIGS. 1A–B, for example, for recovery of the polynucleotide or as a diagnostic probe or as a PCR primer.

Thus, the present invention is directed to polynucleotides having at least a 90% and more preferably at least a 95% identity to a polynucleotide which encodes the polypeptide of FIGS. 1A–B as well as fragments thereof, which fragments have at least 30 bases and preferably at least 50 bases and to polypeptides encoded by such polynucleotides.

In another aspect, the invention provides an isolated nucleic acid molecule comprising a polynucleotide which hybridizes under stringent hybridization conditions to a portion of the polynucleotide in a nucleic acid molecule of the invention described above, for instance, the complement of the CTGF-2 coding polynucleotide sequence disclosed herein or the cDNA clone contained in ATCC Deposit No. 75804. By "stringent hybridization conditions" is intended overnight incubation at 42EC in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 g/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below. In this context "about" includes the particularly recited size, larger or smaller by several (5, 4, 3, 2, or 1) nucleotides, at either terminus or at both termini.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIGS. 1A–B).

Of course, a polynucleotide which hybridizes only to a poly A sequence (such as the 3' terminal poly(A) tract of the CTGF-2 cDNA, or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

In specific embodiments, the polynucleotides of the invention are less than 100000 kb, 50000 kb, 10000 kb, 1000 kb, 500 kb, 400 kb, 350 kb, 300 kb, 250 kb, 200 kb, 175 kb, 150 kb, 125 kb, 100 kb, 75 kb, 50 kb, 40 kb, 30 kb, 25 kb, 20 kb, 15 kb, 10 kb, 7.5 kb, or 5 kb in length.

In further embodiments, polynucleotides of the invention comprise at least 15, at least 30, at least 50, at least 100, or at least 250, at least 500, or at least 1000 contiguous nucleotides of CTGF-2 coding sequence, but consist of less than or equal to 1000 kb, 500 kb, 250 kb, 200 kb, 150 kb, 100 kb, 75 kb, 50 kb, 30 kb, 25 kb, 20 kb, 15 kb, 10 kb, or 5 kb of genomic DNA that flanks the 5' or 3' coding nucleotide set forth in FIGS. 1A–B. In further embodiments, polynucleotides of the invention comprise at least 15, at least 30, at least 50, at least 100, or at least 250, at least 500, or at least 1000 contiguous nucleotides of CTGF-2 coding sequence, but do not comprise all or a portion of any CTGF-2 intron. In another embodiment, the nucleic acid comprising CTGF-2 coding sequence does not contain coding sequences of a genomic flanking gene (i.e., 5' or 3' to the CTGF-2 gene in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

As indicated, nucleic acid molecules of the present invention which encode a CTGF-2 polypeptide may include, but are not limited to the coding sequence for the mature polypeptide, by itself, the coding sequence for the mature polypeptide and additional sequences, such as those encoding a leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al., *Proc. Natl. Acad. Sci. USA* 86: 821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37:767–778 (1984). As discussed below, other such fusion proteins include the CTGF-2 receptor fused to Fc at the N- or C-terminus.

The present invention further relates to variants of the nucleic acid molecules of the present invention, which encode portions, analogs, or derivatives of the CTGF-2 receptor. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions which may involve one or more nucleotides. The variants may be altered in coding or non-coding regions or both. Alterations in the coding regions may produce conservative or non-conservative amino acid substitutions, deletions, or additions. Especially preferred among these are silent substitutions, additions, and deletions, which do not alter the properties and activities of CTGF-2 or portions thereof. Also especially preferred in this regard are conservative substitutions.

Further embodiments of the invention include isolated nucleic acid molecules comprising or, alternatively, consisting of a polynucleotide having a nucleotide sequence at least 80%, 85%, or 90% identical, and more preferably at least 95%, 96%, 97%, 98%, or 99% identical to: (a) a nucleotide sequence encoding the polypeptide having the amino acid sequence in FIGS. 1A–B; (b) a nucleotide sequence encoding the polypeptide having the amino acid sequence in FIGS. 1A–B, but lacking the amino terminal methionine; (c) a nucleotide sequence encoding the polypeptide having the amino acid sequence in FIGS. 1A–B, but lacking the N-terminal leader peptide (i.e. the mature protein); (d) a nucleotide sequence encoding the polypeptide having the amino acid sequence encoded by the cDNA clone contained in ATCC Deposit No. 75804; (e) a nucleotide sequence encoding the mature CTGF-2 polypeptide having the amino acid sequence encoded by the cDNA clone contained in ATCC Deposit No. 75804; (f) a nucleotide sequence encoding the CTGF-2 IGF Binding Domain; (g) a nucleotide sequence encoding the CTGF-2 von Willebrand Factor Type C Repeat Domain; (h) a nucleotide sequence encoding the CTGF-2 Sulfated Glycoconjugate Binding Motif; (i) a nucleotide sequence encoding the CTGF-2 C-Terminal Dimerization and Receptor Binding Domain; and (j) a nucleotide sequence complementary to any of the nucleotide sequences in (a), (b), (c), (d), (e), (f), (g), (h), or (i) above.

By a polynucleotide having a nucleotide sequence at least, for example, 95% "identical" to a reference nucleotide sequence encoding a CTGF-2 polypeptide is intended that the nucleotide sequence of the polynucleotide is identical to the reference sequence except that the polynucleotide sequence may include up to five mismatches per each 100 nucleotides of the reference nucleotide sequence encoding the CTGF-2 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mismatches of the reference sequence may occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be the entire CTGF-2 encoding nucleotide sequence shown in FIGS. 1A–B or any CTGF-2 polynucleotide fragment (e.g., a polynucleotide encoding the amino acid sequence of any of the CTGF-2 N- and/or C-terminal deletions described herein), variant, derivative or analog, as described herein.

As a practical matter, whether any particular nucleic acid molecule is at least 80%, 85%, 90%, 95%, 96%, 97%, 98% or 99% identical to, for instance, the nucleotide sequence shown in FIGS. 1A–B or to the nucleotide sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

The present application is directed to nucleic acid molecules at least 80%, 85%, 90%, 95%, 96%, 97%, 98%, or 99% identical to the nucleic acid sequence for example, shown in FIGS. 1A–B, or to the nucleic acid sequence of the deposited cDNA, irrespective of whether they encode a polypeptide having CTGF-2 activity. This is because even where a particular nucleic acid molecule does not encode a polypeptide having CTGF-2 functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having CTGF-2 activity include, inter alia: (1) isolating the CTGF-2 gene or allelic variants thereof in a cDNA library; (2) in situ hybridization (e.g., "FISH") to metaphase chromosomal spreads to provide precise chromosomal location of the CTGF-2 gene, as described in Verma et al., *Human Chromosomes: A Manual of Basic Techniques*, Pergamon Press, New York (1988); and (3)

Northern Blot analysis for detecting CTGF-2 mRNA expression in specific tissues.

Preferred, however, are nucleic acid molecules having sequences at least 90%, 80%, 85%, 95%, 96%, 97%, 98% or 99% identical to for example, the nucleic acid sequence shown in FIGS. 1A–B, or to the nucleic acid sequence of the deposited cDNA, which do, in fact, encode a polypeptide having CTGF-2 functional activity. By "a polypeptide having CTGF-2 functional receptor activity" is intended polypeptides exhibiting activity similar, but not necessarily identical, to an activity of the CTGF-2 of the invention (either the full-length protein or, preferably, the mature protein), as measured in a particular biological assay. For example CTGF-2 functional receptor activity can be measured using the cell proliferation or angiogenesis assays performed essentially as previously described in the Examples, below.

Of course, due to the degeneracy of the genetic code, one of ordinary skill in the art will immediately recognize that a large number of the nucleic acid molecules having a sequence at least 80%, 85%, 90%, 95%, 96%, 97%, 98%, or 99% identical to, for example, the nucleic acid sequence of the deposited cDNA or the nucleic acid sequence shown in FIGS. 1A–B will encode a polypeptide "having CTGF-2 functional activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having CTGF-2 activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in J. U. Bowie et al., "Deciphering the Message in Protein Sequences: Tolerance to Amino Acid Substitutions," *Science* 247.1306–1310 (1990), wherein the authors indicate that proteins are surprisingly tolerant of amino acid substitutions.

Protein/Polypeptide Embodiments

The present invention further relates to a polypeptide which has the deduced amino acid sequence of FIGS. 1A–B or which has the amino acid sequence encoded by the deposited cDNA, as well as fragments, analogs and derivatives of such polypeptide.

The terms "fragment," "derivative" and "analog" when referring to the polypeptide of FIGS. 1A–B or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIGS. 1A–B or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the full-length polypeptide, the mature polypeptide, as well as polypeptides which have at least 70% similarity (preferably at least 70% identity) to the polypeptide of FIGS. 1A–B and more preferably at least 90% similarity (more preferably at least 90% identity) to the polypeptide of FIGS. 1A–B and still more preferably at least 95% similarity (still more preferably at least 95% identity) to the polypeptide of FIGS. 1A–B and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

To improve or alter the characteristics of CTGF-2 polypeptides, protein engineering may be employed. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions. For instance, for many proteins, including the extracellular domain or the mature form(s) of a secreted protein, it is known in the art that one or more amino acids may be deleted from the N-terminus or C-terminus without substantial loss of biological function. For instance, Ron et al., J. Biol. Chem., 268:2984–2988 (1993) reported modified KGF proteins that had heparin binding activity even if 3, 8, or 27 amino-terminal amino acid residues were missing.

In the present case, deletions of N-terminal amino acids up to the Ile(I) residue at position 376 in FIGS. 1A–B may retain some biological activity. The amino acids constituting the IGF-Binding Domain, von Willebrand Factor Type C Repeat Domain, Sulfated Glycoconjugated Binding Motif, and C-Terminal Dimerization and Receptor Binding Domain of the CTGF-2 protein are described above. However, even if deletion of one or more amino acids from the N-terminus of a protein results in modification of loss of one or more biological functions of the protein, other functional activities may still be retained. Thus, the ability of the shortened protein to induce and/or bind to antibodies which recognize the complete or extracellular domain of the protein generally will be retained when less than the majority of the residues of the complete or extracellular domain of the protein are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues from the amino terminus of the amino acid sequence of the CTGF-2 shown in FIGS. 1A–B, up to the isoleucine residue at position 376 (Ile-376 residue from the amino terminus), and polynucleotides encoding such polypeptides. In particular, the present invention provides polypeptides having the amino acid sequence of residues $n^1$-381 of FIGS. 1A–B, where $n^1$ is an integer in the range of the amino acid position of amino acid residues 2–376 of the amino acid sequence in FIGS. 1A–B. More in particular, the invention provides polynucleotides encoding polypeptides comprising, or alternatively consisting of, an amino acid sequence selected from the group consisting of residues S-2 to D-381; S-3 to D-381; R-4 to D-381; I-5 to D-381; A-6 to D-381; R-7 to D-381; A-8 to D-381; L-9 to D-381; A-10 to D-381; L-11 to D-381; V-12 to D-381; V-13 to D-381; T-14 to D-381; L-15 to D-381; L-16 to D-381; H-17 to D-381; L-18 to D-381; T-19 to D-381; R-20 to D-381; L-21 to D-381; A-22 to D-381; L-23 to D-381; S-24 to D-381; T-25 to D-381; C-26 to D-381; P-27 to D-381; A-28 to D-381; A-29 to D-381; C-30 to D-381; H-31 to D-381; C-32 to D-381; P-33 to D-381; L-34 to D-381; E-35 to D-381; A-36 to D-381; P-37 to D-381; K-38 to D-381; C-39 to D-381; A-40 to D-381; P-41 to D-381; G-42 to D-381; V-43 to D-381; G-44 to D-381; L-45 to D-381; V-46 to D-381; R-47 to D-381; D-48 to D-381; G-49 to D-381; C-50 to D-381; G-51 to D-381; C-52 to D-381; C-53 to D-381; K-54 to D-381; V-55 to D-381; C-56 to D-381; A-57 to D-381; K-58 to D-381; Q-59 to D-381; L-60 to D-381; N-61 to D-381; E-62 to D-381; D-63 to D-381; C-64 to D-381; S-65 to D-381; K-66 to D-381; T-67 to D-381; Q-68 to D-381; P-69 to D-381; C-70 to D-381; D-71 to D-381; H-72 to D-381; T-73 to D-381; K-74 to D-381; G-75 to D-381; L-76 to D-381; E-77 to D-381; C-78 to D-381; N-79 to D-381; F-80 to D-381; G-81 to D-381; A-82 to D-381; S-83 to D-381; S-84 to D-381; T-85 to D-381; A-86 to D-381; L-87 to D-381; K-88 to D-381; G-89 to D-381; I-90 to D-381; C-91 to D-381; R-92 to D-381; A-93 to D-381; Q-94 to D-381; S-95 to D-381; E-96 to D-381; G-97 to D-381; R-98 to D-381; P-99 to D-381; C-100 to D-381; E-101 to D-381; Y-102 to D-381; N-103 to D-381; S-104 to D-381; R-105 to D-381; I-106 to D-381; Y-107 to D-381; Q-108 to D-381; N-109 to D-381; G-110 to D-381; E-111 to D-381; S-112 to D-381; F-113 to D-381; Q-114 to D-381; P-115 to D-381; N-116 to D-381; C-117 to D-381; K-118 to D-381; H-119 to D-381; Q-120 to D-381; C-121 to D-381; T-122 to D-381; C-123 to D-381; I-124 to D-381; D-125 to D-381; G-126 to D-381; A-127 to D-381; V-128 to D-381; G-129 to D-381; C-130 to D-381; I-131 to D-381; P-132 to D-381; L-133 to D-381; C-134 to D-381; P-135 to D-381; Q-136 to D-381; E-137 to D-381; L-138 to D-381; S-139 to D-381; L-140 to D-381; P-141 to D-381; N-142 to D-381; L-143 to D-381; G-144 to D-381; C-145 to D-381; P-146 to D-381; N-147 to D-381; P-148 to D-381; R-149 to D-381; L-150 to D-381; V-151 to D-381; K-152 to D-381; V-153 to D-381; T-154 to D-381; G-155 to D-381; Q-156 to D-381; C-157 to D-381; C-158 to D-381; E-159 to D-381; E-160 to D-381; W-161 to D-381; V-162 to D-381; C-163 to D-381; D-164 to D-381; E-165 to D-381; D-166 to D-381; S-167 to D-381; I-168 to D-381; K-169 to D-381; D-170 to D-381; P-171 to D-381; M-172 to D-381; E-173 to D-381; D-174 to D-381; Q-175 to D-381; D-176 to D-381; G-177 to D-381; L-178 to D-381; L-179 to D-381; G-180 to D-381; K-181 to D-381; E-182 to D-381; L-183 to D-381; G-184 to D-381; F-185 to D-381; D-186 to D-381; A-187 to D-381; S-188 to D-381; E-189 to D-381; V-190 to D-381; E-191 to D-381; L-192 to D-381; T-193 to D-381; R-194 to D-381 N-195 to D-381; N-196 to D-381; E-197 to D-381; L-198 to D-381; I-199 to D-381; A-200 to D-381; V-201 to D-381; G-202 to D-381; K-203 to D-381; G-204 to D-381; S-205 to D-381; S-206 to D-381; L-207 to D-381; K-208 to D-381; R-209 to D-381; L-210 to D-381; P-211 to D-381; V-212 to D-381; F-213 to D-381; G-214 to D-381; M-215 to D-381; E-216 to D-381; P-217 to D-381; R-218 to D-381; I-219 to D-381; L-220 to D-381; Y-221 to D-381; N-222 to D-381; P-223 to D-381; L-224 to D-381; Q-225 to D-381; G-226 to D-381; Q-227 to D-381; K-228 to D-381; C-229 to D-381; I-230 to D-381; V-231 to D-381; Q-232 to D-381; T-233 to D-381; T-234 to D-381; S-235 to D-381; W-236 to D-381; S-237 to D-381; Q-238 to D-381; C-239 to D-381; S-240 to D-381; K-241 to D-381; T-242 to D-381; C-243 to D-381; G-244 to D-381; T-245 to D-381; G-246 to D-381; I-247 to D-381; S-248 to D-381; T-249 to D-381; R-250 to D-381; V-251 to D-381; T-252 to D-381; N-253 to D-381; D-254 to D-381; N-255 to D-381; P-256 to D-381; E-257 to D-381; C-258 to D-381; R-259 to D-381; L-260 to D-381; V-261 to D-381; K-262 to D-381; E-263 to D-381; T-264 to D-381; R-265 to D-381; I-266 to D-381; C-267 to D-381; E-268 to D-381; V-269 to D-381; R-270 to D-381; P-271 to D-381; C-272 to D-381; G-273 to D-381; Q-274 to D-381; P-275 to D-381; V-276 to D-381; Y-277 to D-381; S-278 to D-381; S-279 to D-381; L-280 to D-381; K-281 to D-381; K-282 to D-381; G-283 to D-381; K-284 to D-381; K-285 to D-381; C-286 to D-381; S-287 to D-381; K-288 to D-381; T-289 to D-381; K-290 to D-381; K-291 to D-381; S-292 to D-381; P-293 to D-381; E-294 to D-381; P-295 to D-381; V-296 to D-381; R-297 to D-381; F-298 to D-381; T-299 to D-381; Y-300 to D-381; A-301 to D-381; G-302 to D-381; C-303 to D-381; L-304 to D-381; S-305 to D-381; V-306 to D-381; K-307 to D-381; K-308 to D-381; Y-309 to D-381; R-310 to D-381; P-311 to D-381; K-312 to D-381; Y-313 to D-381; C-314 to D-381; G-315 to D-381; S-316 to D-381; C-317 to D-381; V-318 to D-381; D-319 to D-381; G-320 to D-381; R-321 to D-381; C-322 to D-381; C-323 to D-381; T-324 to D-381; P-325 to D-381; Q-326 to D-381; L-327 to D-381; T-328 to D-381; R-329 to D-381; T-330 to D-381; V-331 to D-381; K-332 to D-381; M-333 to D-381; R-334 to D-381; F-335 to D-381; R-336 to D-381; C-337 to D-381; E-338 to D-381; D-339 to D-381; G-340 to D-381; E-341 to D-381; T-342 to D-381; F-343 to D-381; S-344 to D-381; K -345 to D-381; N -346 to D-381; V-347 to D-381; M-348 to D-381; M-349 to D-381; I-350 to D-381; Q-351 to D-381; S-352 to D-381; C-353 to D-381; K-354 to D-381; C-355 to D-381; N-356 to D-381; Y-357 to D-381; N-358 to D-381; C-359 to D-381; P-360 to D-381; H-361 to D-381; A-362 to D-381; N-363 to D-381; E-364 to D-381; A-365 to D-381; A-366 to D-381; F-367 to D-381; P-368 to D-381; F-369 to D-381; Y-370 to D-381; R-371 to D-381; L-372 to D-381; F-373 to D-381; N-374 to D-381; D-375 to D-381; I-376 to D-381 of FIGS. 1A–B. The present application is also directed to nucleic acid molecules comprising, or alternatively, consisting of, a polynucleotide sequence at least 90%, 92%, 95%, 96%, 97%, 98% or 99% identical to the polynucleotide sequence encoding the CTGF-2 polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising an amino acid sequence at least 90%, 92%, 95%, 96%, 97%, 98% or 99% identical to the amino acid sequence described above, and polynucleotides that encode such polypeptides.

Similarly, many examples of biologically functional C-terminal deletion muteins are known. For instance, Interferon gamma shows up to ten times higher activities by deleting 8–10 amino acid residues from the carboxy terminus of the protein (Döbeli et al., *J. Biotechnology* 7:199–216 (1988). However, even if deletion of one or more amino acids from the C-terminus of a protein results in modification of loss of one or more biological functions of the protein, other functional activities may still be retained. Thus, the ability of the shortened protein to induce and/or bind to antibodies which recognize the complete or mature protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art.

Accordingly, the present invention further provides polypeptides having one or more residues from the carboxy terminus of the amino acid sequence of the CTGF-2 shown in FIGS. 1A–B, up to the histidine residue at position 361 (His-361) and polynucleotides encoding such polypeptides. In particular, the present invention provides polypeptides having the amino acid sequence of residues 1-m$^1$ of the amino acid sequence in FIGS. 1A–B, where m$^1$ is any integer in the range of the amino acid position of amino acid residues 6 to 380 in FIGS. 1A–B. More in particular, the invention provides polynucleotides encoding polypeptides comprising, or alternatively consisting of, an amino acid sequence selected from the group consisting of residues M-1 to R-380; M-1 to F-379; M-1 to K-378; M-1 to H-377; M-1 to I-376; M-1 to D-375; M-1 to N-374; M-1 to F-373; M-1 to L-372; M-1 to R-371; M-1 to Y-370; M-1 to F-369; M-1 to P-368; M-1 to F-367; M-1 to A-366; M-1 to A-365; M-1 to E-364; M-1 to N-363; M-1 to A-362; M-1 to H-361; M-1 to P-360; M-1 to C-359; M-1 to N-358; M-1 to Y-357; M-1 to N-356; M-1 to C-355; M-1 to K-354; M-1 to C-353; M-1 to S-352; M-1 to Q-351; M-1 to I-350; M-1 to M-349; M-1 to M-348; M-1 to V-347; M-1 to N-346; M-1 to K-345; M-1 to S-344; M-1 to F-343; M-1 to T-342; M-1 to E-341; M-1 to G-340; M-1 to D-339; M-1 to E-338; M-1 to C-337; M-1 to R-336; M-1 to F-335; M-1 to R-334; M-1 to M-333; M-1 to K-332; M-1 to V-331; M-1 to T-330; M-1 to R-329; M-1 to T-328; M-1 to L-327; M-1 to Q-326; M-1 to P-325; M-1 to T-324; M-1 to C-323; M-1 to C-322; M-1 to R-321; M-1 to G-320; M-1 to D-319; M-1 to V-318; M-1 to C-317; M-1 to S-316; M-1 to G-315; M-1 to C-314; M-1 to Y-313; M-1 to K-312; M-1 to P-311; M-1 to R-310; M-1 to Y-309; M-1 to K-308; M-1 to K-307; M-1 to V-306; M-1 to S-305; M-1 to L-304; M-1 to C-303; M-1 to G-302; M-1 to A-301; M-1 to Y-300; M-1 to T-299; M-1 to F-298; M-1 to R-297; M-1 to V-296; M-1 to P-295; M-1 to E-294; M-1 to P-293; M-1 to S-292; M-1 to K-291; M-1 to K-290; M-1 to T-289; M-1 to K-288; M-1 to S-287; M-1 to C-286; M-1 to K-285; M-1 to K-284; M-1 to G-283; M-1 to K-282; M-1 to K-281; M-1 to L-280; M-1 to S-279; M-1 to S-278; M-1 to Y-277; M-1 to V-276; M-1 to P-275; M-1 to Q-274; M-1 to G-273; M-1 to C-272; M-1 to P-271; M-1 to R-270; M-1 to V-269; M-1 to E-268; M-1 to C-267; M-1 to I-266; M-1 to R-265; M-1 to T-264; M-1 to E-263; M-1 to K-262; M-1 to V-261; M-1 to L-260; M-1 to R-259; M-1 to C-258; M-1 to E-257; M-1 to P-256; M-1 to N-255; M-1 to D-254; M-1 to N-253; M-1 to T-252; M-1 to V-251; M-1 to R-250; M-1 to T-249; M-1 to S-248; M-1 to 1–247; M-1 to G-246; M-1 to T-245; M-1 to G-244; M-1 to C-243; M-1 to T-242; M-1 to K-241; M-1 to S-240; M-1 to C-239; M-1 to Q-238; M-1 to S-237; M-1 to W-236; M-1 to S-235; M-1 to T-234; M-1 to T-233; M-1 to Q-232; M-1 to V-231; M-1 to I-230; M-1 to C-229; M-1 to K-228; M-1 to Q-227; M-1 to G-226; M-1 to Q-225; M-1 to L-224; M-1 to P-223; M-1 to N-222; M-1 to Y-221; M-1 to L-220; M-1 to I-219; M-1 to R-218; M-1 to P-217; M-1 to E-216; M-1 to M-215; M-1 to G-214; M-1 to F-213; M-1 to V-212; M-1 to P-211; M-1 to L-210; M-1 to R-209; M-1 to K-208; M-1 to L-207; M-1 to S-206; M-1 to S-205; M-1 to G-204; M-1 to K-203; M-1 to G-202; M-1 to V-201; M-1 to A-200; M-1 to I-199; M-1 to L-198; M-1 to E-197; M-1 to N-196; M-1 to N-195; M-1 to R-194; M-1 to T-193; M-1 to L-192; M-1 to E-191; M-1 to V-190; M-1 to E-189; M-1 to S-188; M-1 to A-187; M-1 to D-186; M-1 to F-185; M-1 to G-184; M-1 to L-183; M-1 to E-182; M-1 to K-181; M-1 to G-180; M-1 to L-179; M-1 to L-178; M-1 to G-177; M-1 to D-176; M-1 to Q-175; M-1 to D-174; M-1 to E-173; M-1 to M-172; M-1 to P-171; M-1 to D-170; M-1 to K-169; M-1 to I-168; M-1 to S-167; M-1 to D-166; M-1 to E-165; M-1 to D-164; M-1 to C-163; M-1 to V-162; M-1 to W-161; M-1 to E-160; M-1 to E-159; M-1 to C-158; M-1 to C-157; M-1 to Q-156; M-1 to G-155; M-1 to T-154; M-1 to V-153; M-1 to K-152; M-1 to V-151; M-1 to L-150; M-1 to R-149; M-1 to P-148; M-1 to N-147; M-1 to P-146; M-1 to C-145; M-1 to G-144; M-1 to L-143; M-1 to N-142; M-1 to P-141; M-1 to L-140; M-1 to S-139; M-1 to L-138; M-1 to E-137; M-1 to Q-136; M-1 to P-135; M-1 to C-134; M-1 to L-133; M-1 to P-132; M-1 to I-131; M-1 to C-130; M-1 to G-129; M-1 to V-128; M-1 to A-127; M-1 to G-126; M-1 to D-125; M-1 to I-124; M-1 to C-123; M-1 to T-122; M-1 to C-121; M-1 to Q-120; M-1 to H-119; M-1 to K-118; M-1 to C-117; M-1 to N-116; M-1 to P-115; M-1 to Q-114; M-1 to F-113; M-1 to S-112; M-1 to E-111; M-1 to G-110; M-1 to N-109; M-1 to Q-108; M-1 to Y-107; M-1 to I-106; M-1 to R-105; M-1 to S-104; M-1 to N-103; M-1 to Y-102; M-1 to E-101; M-1 to C-100; M-1 to P-99; M-1 to R-98; M-1 to G-97; M-1 to E-96; M-1 to S-95; M-1 to Q-94; M-1 to A-93; M-1 to R-92; M-1 to C-91; M-1 to I-90; M-1 to G-89; M-1 to K-88; M-1 to L-87; M-1 to A-86; M-1 to T-85; M-1 to S-84; M-1 to S-83; M-1 to A-82; M-1 to G-81; M-1 to F-80; M-1 to N-79; M-1 to C-78; M-1 to E-77; M-1 to L-76; M-1 to G-75; M-1 to K-74; M-1 to T-73; M-1 to H-72; M-1 to D-71; M-1 to C-70; M-1 to P-69; M-1 to Q-68; M-1 to T-67; M-1 to K-66; M-1 to S-65; M-1 to C-64; M-1 to D-63; M-1 to E-62; M-1 to N-61; M-1 to L-60; M-1 to Q-59; M-1 to K-58; M-1 to A-57; M-1 to C-56; M-1 to V-55; M-1 to K-54; M-1 to C-53; M-1 to C-52; M-1 to G-51; M-1 to C-50; M-1 to G-49; M-1 to D-48; M-1 to R-47; M-1 to V-46; M-1 to L-45; M-1 to G-44; M-1 to V-43; M-1 to G-42; M-1 to P-41; M-1 to A-40; M-1 to C-39; M-1 to K-38; M-1 to P-37; M-1 to A-36; M-1 to E-35; M-1 to L-34; M-1 to P-33; M-1 to C-32; M-1 to H-31; M-1 to C-30; M-1 to A-29; M-1 to A-28; M-1 to P-27;

M-1 to C-26; M-1 to T-25; M-1 to S-24; M-1 to L-23; M-1 to A-22; M-1 to L-21; M-1 to R-20; M-1 to T-19; M-1 to L-18; M-1 to H-17; M-1 to L-16; M-1 to L-15; M-1 to T-14; M-1 to V-13; M-1 to V-12; M-1 to L-11; M-1 to A-10; M-1 to L-9; M-1 to A-8; M-1 to R-7; M-1 to A-6 of FIGS. 1A–B. The present application is also directed to nucleic acid molecules comprising, or alternatively, consisting of, a polynucleotide sequence at least 90%, 92%, 95%, 96%, 97%, 98% or 99% identical to the polynucleotide sequence encoding the CTGF-2 polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising an amino acid sequence at least 90%, 92%, 95%, 96%, 97%, 98% or 99% identical to the amino acid sequence described above, and polynucleotides that encode such polypeptides.

Also provided are polypeptides having one or more amino acids deleted from both the amino and the carboxyl termini, which may be described generally as having residues $n^1$-$m^1$ of FIGS. 1A–B, where $n^1$ and $m^1$ are integers as defined above. Also included are a nucleotide sequence encoding a polypeptide consisting of a portion of the complete CTGF-2 amino acid sequence encoded by the deposited cDNA clone contained in ATCC Accession No. 75804 where this portion excludes from 1 to 376 amino acids from the amino terminus or from 1 to 380 amino acids from the C-terminus of the complete amino acid sequence (or any combination of these N-terminal and C-terminal deletions) encoded by the cDNA clone in the deposited clone. Polynucleotides encoding all of the above deletion polypeptides are encompassed by the invention.

Epitopes

In specific embodiments polypeptides of the present invention comprise, or alternatively consist of, one, two, three, four, five, six, seven, eight, nine, ten, eleven, twelve, thirteen, fourteen, or all fourteen of the immunogenic epitopes of the CTGF-2 protein shown in FIGS. 1A–B as residues: Glu-35 to Pro-41, Arg-47 to Gly-51, Gln-59 to Gly-75, Cys-91 to His-119, Cys-145 to Leu-150, Asp-164 to Asp-176, Gly-202 to Lys-208, Pro-223 to Lys-228, Cys-239 to Gly-244, Arg-250 to Glu-257, Ser-279 to Val-296, Lys-307 to Cys-314, Val-318 to Cys-323, and Cys-337 to Phe-343. Fragments and/or variants of these polypeptides, such as, for example, fragments and/or variants as described herein, are encompassed by the invention. Polynucleotides encoding these polypeptides (including fragments and/or variants) are also encompassed by the invention, as are antibodies that bind these polypeptides.

The present invention encompasses polypeptides comprising, or alternatively consisting of, an epitope of the polypeptide having an amino acid sequence of FIGS. 1A–B, or an epitope of the polypeptide sequence encoded by a polynucleotide sequence contained in deposited clone (ATCC accession no. 75804) or encoded by a polynucleotide that hybridizes to the complement of the sequence of FIGS. 1A–B or contained in deposited clone (ATCC accession no. 75804) under stringent hybridization conditions or lower stringency hybridization conditions as defined supra. The present invention further encompasses polynucleotide sequences encoding an epitope of a polypeptide sequence of the invention (such as, for example, the sequence disclosed in FIGS. 1A–B), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments that function as epitopes may be produced by any conventional means. (See, e.g., Houghten, Proc. Natl. Acad. Sci. USA 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at 15, at least 20, at least 25, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Antigenic epitopes are useful, for example, to raise antibodies, including monoclonal antibodies, that specifically bind the epitope. Antigenic epitopes can be used as the target molecules in immunoassays. (See, for instance, Wilson et al., Cell 37:767–778 (1984); Sutcliffe et al., *Science* 219:660–666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). The polypeptides comprising one or more immunogenic epitopes may be presented for eliciting an antibody response together with a carrier protein, such as an albumin, to an animal system (such as, for example, rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as, for example, rabbits, rats, and mice are immunized with either free or carrier-coupled peptides, for instance, by intraperitoneal and/or intradermal injection of emulsions containing about 100 micrograms of peptide or carrier protein and Freund's adjuvant or any other adjuvant known for stimulating an immune response. Several booster injections may be needed, for instance, at intervals of about two weeks, to provide a useful titer of anti-peptide antibody that can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86 (1988). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues. The tag serves as a matrix-binding domain for the fusion protein. Extracts from cells infected with the recombinant vaccinia virus are loaded onto $Ni^{2+}$ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724–33 (1997); Harayama, Trends Biotechnol. 16(2):76–82 (1998); Hansson, et al., J. Mol. Biol. 287:265–76 (1999); and Lorenzo and Blasco, Biotechniques 24(2):308–13 (1998) (each of these patents and publications are hereby incorporated by reference in its entirety). In one embodiment, alteration of polynucleotides corresponding to FIGS. 1A–B and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide coding a polypeptide of the invention may be recombined with one or more components, motifs, sections, parts, domains, fragments, etc. of one or more heterologous molecules.

Antibodies

The present invention further relates to antibodies and T-cell antigen receptors (TCR) which immunospecifically bind a polypeptide, preferably an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab?) fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine, donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention that they recognize or specifically bind. The epitope(s) or polypeptide portion(s) may be specified as described herein, e.g., by N-terminal and C-terminal positions, by size in contiguous amino acid residues, or listed in the Tables and Figures. Antibodies that specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies that bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10^{-2}$M, $10^{-2}$M, $5\times10^{-3}$M, $10^{-3}$M, $5\times10^{-4}$M, $10^{-4}$M, $5\times10^{-5}$M, $10^{-5}$M, $5\times10^{-6}$M, $10^{-6}$M, $5\times10^{-7}$M, $10^{-7}$M, $5\times10^{-8}$M, $10^{-8}$ M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 90%, at least 80%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand or receptor activity by at least 90%, at least 80%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981–1988 (1998); Chen, et al., Cancer Res. 58(16):3668–3678 (1998); Harrop et al., J. Immunol. 161(4):1786–1794 (1998); Zhu et al., Cancer Res. 58(15):3209–3214 (1998); Yoon, et al., J. Immunol. 160(7):3170–3179 (1998); Prat et al., J. Cell. Sci. 111(Pt2):237–247 (1998); Pitard et al., J. Immunol. Methods 205(2):177–190 (1997); Liautard et al., Cytokine 9(4):233–241 (1997); Carlson et al., J. Biol. Chem. 272(17):11295–11301 (1997); Taryman et al., Neuron 14(4):755–762 (1995); Muller et al., Structure 6(9):1153–1167 (1998); Bartunek et a Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well-known in the art. Briefly, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41–50 (1995); Ames et al., J. Immunol. Methods 184:177–186 (1995); Kettleborough et al., Eur. J. Immunol. 24:952–958 (1994); Persic et al., Gene 187 9–18 (1997); Burton et al., Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI 34:26–34 (1995); and Better et al., Science 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; U.S. Pat. Nos. 5,807,715; 4,816,567; and 4,816397, which are incorporated herein by reference in their entireties. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530, 101; and 5,585,089), veneering or resurfacing (EP 592,106; EP 519,596; Padlan, Molecular Immunology 28(4/5) :489–498 (1991); Studnicka et al., Protein Engineering 7(6):805–814 (1994); Roguska. et al., PNAS 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716, 111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65–93). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of FIGS. 1A–B.

Such polynucleotides are used in accordance with the invention both to produce antibodies for isolation, and as components for use in antibody-based gene therapy regimens. Thus, these polynucleotides can be used in according to the procedures for using CTGF-2 encoding polynucleotides in gene therapy as described in detail below.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., Bio-Techniques 17:242 (1994)), which, briefly, involves the synthesis of overlapping oligonucleotides containing portions of the sequence encoding the antibody, annealing and ligation of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be obtained from a suitable source (e.g., an antibody cDNA library, or a cDNA library generated from, or nucleic acid, preferably poly A+RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties ), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278:457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., 1984, Proc. Natl. Acad. Sci. 81:851–855; Neuberger et al., 1984, Nature 312:604–608; Takeda et al., 1985, Nature 314:452–454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,694,778; Bird, 1988, Science 242:423–42; Huston et al., 1988, Proc. Natl. Acad. Sci. USA 85:5879–5883; and Ward et al., 1989, Nature 334:544–54) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., 1988, Science 242:1038–1041).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, e.g., a heavy or light chain of an antibody of the invention, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., E. coli, B. subtilis) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; Cockett et al., 1990, Bio/Technology 8:2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, 1985, Nucleic Acids Res. 13:3101–3109; Van Heeke & Schuster, 1989, J. Biol. Chem. 24:5503–5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in Spodoptera frugiperda cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, 1984, Proc. Natl. Acad. Sci. USA 81:355–359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:51–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., 1977, Cell 11:223), hypoxanthine-guanine phosphoribosyltransferase (Szybalski & Szybalski, 192, Proc. Natl. Acad. Sci. USA 48:202), and adenine phosphoribosyltransferase (Lowy et al., 1980, Cell 22:817) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 Clinical Pharmacy 12:488–505; Wu and Wu, 1991, Biotherapy 3:87–95; Tolstoshev, 1993, Ann. Rev.

Pharmacol. Toxicol. 32:573–596; Mulligan, 1993, Science 260:926–932; and Morgan and Anderson, 1993, Ann. Rev. Biochem. 62:191–217; May, 1993, TIB TECH 11(5) :155–215); and hygro, which confers resistance to hygromycin (Santerre et al., 1984, Gene 30:147). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY; Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, Nature 322:52; Kohler, 1980, Proc. Natl. Acad. Sci. USA 77:2197). The coding sequences for the heavy and light chains may comprise cDNA or genomic DNA.

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins.

Antibody Conjugates

The present invention encompasses antibodies recombinantly fused or chemically conjugated (including both covalently and non-covalently conjugations) to a polypeptide (or portion thereof, preferably at least 10, 20 or 50 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20 or 50 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

Figure 2:
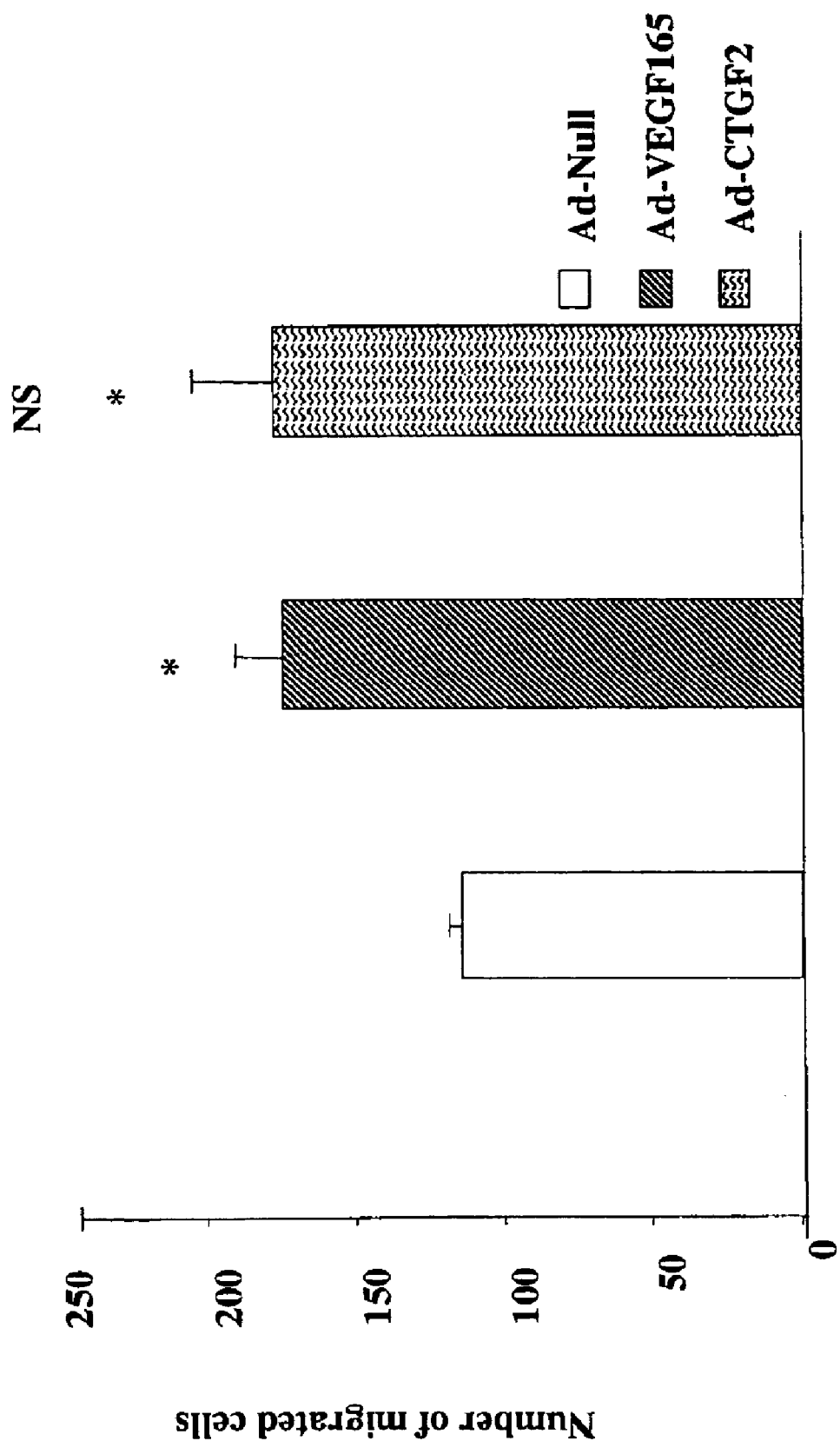
FIG. 2: Migration of HDMEC across 5-μm pore size Transwell migration chamber incubated with supernatant of cells infected with Ad-Null, Ad-VEGF$_{165}$ or Ad-CTGF-2. In a comparable manner, Ad-CTGF-2 and Ad-VEGF$_{165}$-infected cells supernatant significantly stimulated the migration of HDMEC compared with Ad-Null.

Polypeptides of the invention (including antibodies of the invention, see below) may also be fused to albumin (including but not limited to recombinant human serum albumin (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)), resulting in chimeric polypeptides. In a preferred embodiment, polypeptides (including antibodies) of the present invention (including fragments or variants thereof) are fused with the mature form of human serum albumin (i.e., amino acids 1–585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Such human serum albumin-CTGF-2 fusion proteins may be used therapeutically in accordance with the invention to stimulate, for example, angiogenesis as indicated below with respect to adenoviral-vector delivered DNA encoding CTGF-2.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides of the present invention may be fused or conjugated to the above antibody portions to increase the in vivo half life of the polypeptides or for use in immunoassays using methods known in the art. Further, the polypeptides of the present invention may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270:9459–9471 (1995)0.

Moreover, the antibodies or fragments thereof of the present invention can be fused to marker sequences, such as a peptide to facilitates their purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the HA tag, which corresponds to an epitope derived from the influenza hemagglutinin protein (Wilson et al., Cell 37:767 (1984)) and the flag tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

Further, an antibody or fragment thereof may be conjugated to a therapeutic moiety such as a cytotoxin, e.g., a cytostatic or cytocidal agent, a therapeutic agent or a radioactive metal ion. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Inmunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Assays For Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest is conjugated to a labeled compound (e.g., $^3$H or $^{125}$I) in the presence of increasing amounts of an unlabeled second antibody.

Therapeutic Uses

The present invention is further directed to antibody-based therapies which involve administering antibodies (e.g., CTGF-2 antagonists) of the invention to an animal, preferably a mammal, and most preferably a human, patient for treating one or more of the described disorders. Therapeutic compounds of the invention include, but are not limited to, antibodies of the invention (including fragments, analogs and derivatives thereof as described herein) and nucleic acids encoding antibodies of the invention (including fragments, analogs and derivatives thereof as described herein). The antibodies of the invention can be used to treat, inhibit or prevent diseases and disorders associated with aberrant expression and/or activity of a polypeptide of the invention, including, but not limited to, inhibition of angiogenesis, as discussed in detail below. The treatment and/or prevention of diseases and disorders associated with aberrant expression and/or activity of a polypeptide of the invention includes, but is not limited to, alleviating symptoms associated with those diseases and disorders. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

Gene Therapy

The novel use of CTGF-2 encoding DNA in the stimulation of angiogenesis by gene therapy, in accordance with the invention, is disclosed herein. (See, e.g., Example 12 below).

In accordance with the invention, nucleic acids comprising sequences encoding CTGF-2 or functional derivatives thereof, are administered to stimulate angiogenesis. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11(5):155–215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred aspect, the compound comprises nucleic acid sequences encoding CTGF-2 or polypeptide having CTGF-2 activity as described above, said nucleic acid sequences being part of expression vectors that express the CTGF-2 protein or derivative in a suitable host. In particular, such nucleic acid sequences have promoters operably linked to the antibody coding region, said promoter being inducible or constitutive, and, optionally, tissue-specific. In another particular embodiment, nucleic acid molecules are used in which the CTGF-2 coding sequences and any other desired sequences are flanked by regions that promote homologous recombination at a desired site in the genome, thus providing for intrachromosomal expression of the antibody nucleic acids (Koller and Smithies, 1989, Proc. Natl. Acad. Sci. USA 86:8932–8935; Zijlstra et al., 1989, Nature 342:435–438). The expressed polynucleotides of the invention described in detail, above.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262:4429–4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342:435–438).

In a specific embodiment, viral vectors that contains nucleic acid sequences encoding a CTGF-2 polypeptide of the invention are used. For example, a retroviral vector can be used (see Miller et al., 1993, Meth. Enzymol. 217:581–599). These retroviral vectors have been to delete retroviral sequences that are not necessary for packaging of the viral genome and integration into host cell DNA. The nucleic acid sequences encoding the antibody to be used in gene therapy are cloned into one or more vectors, which facilitates delivery of the gene into a patient. More detail about retroviral vectors can be found in Boesen et al., 1994, Biotherapy 6:291–302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel. 3:110–114.

Adenoviruses are other viral vectors that can be used in gene therapy as detailed in a preferred embodiment in Example 12, below. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499–503 present a review of adenovirus-based gene therapy. Bout et al., 1994, Human Gene Therapy 5:3–10 demonstrated the use of adenovirus vectors to transfer genes to the respiratory epithelia of rhesus monkeys. Other instances of the use of adenoviruses in gene therapy can be found in Rosenfeld et al., 1991, Science 252:431–434; Rosenfeld et al., 1992, Cell 68:143–155; Mastrangeli et al., 1993, J. Clin. Invest. 91:225–234; PCT Publication WO94/12649; and Wang, et al., 1995, Gene Therapy 2:775–783, each of which is hereby incorporated by reference in its entirety. In a preferred embodiment, adenovirus vectors are used.

In a specific, preferred embodiment, the CTGF-2 cDNA of ATCC deposit no. 75804 is cloned into the BamHI restriction site of Bluescript vector (Stratagene), and then is EcoRI/XbaI subcloned in a transfer vector containing the CMV promoter. An E1/E3 deleted AdCTGF-2 vector is obtained by homologous recombination in 293 cells between the transfer vector and the genomic ClaI DNA fragment isolated from the H5d1324 virus. The recombinant virus is plaque purified and amplified on 293 cells, and genome virus integrity is analyzed by restriction enzyme digestion and Southern blot. Titres of infectious viral progeny are determined as infectious units (IU) by quantitative DBP immunofluorescence.

Adeno-associated virus (AAV) has also been proposed for use in gene therapy (Walsh et al., 1993, Proc. Soc. Exp. Biol. Med. 204:289–300; U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, Meth. Enzymol. 217:599–618; Cohen et al., 1993, Meth. Enzymol. 217:618–644; Cline, 1985, Pharmac. Ther. 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy are prefereably endothelial cells, but encompass any desired, available cell type, and include but are not limited to epithelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598, dated Apr. 28, 1994; Stemple and Anderson, 1992, Cell 71:973–985; Rheinwald, 1980, Meth. Cell Bio. 21A:229; and Pittelkow and Scott, 1986, Mayo Clinic Proc. 61:771).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Expression, Production, and Screening

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Streptomyces, Salmonella typhimurium*; fungal cells, such as yeast; insect cells such as *Drosophila S2* and *Spodoptera Sf9*; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), á-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, a polyadenylation site, splice donor and acceptor sites, transcriptional termination sequences, and 5' flanking nontranscribed sequences. DNA sequences derived from the SV40 splice, and Fret polyadenylation sites may be used to provide the required nontranscribed genetic elements.

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated.

Polypeptides of the invention may also include an initial methionine amino acid residue.

This invention provides a method for identification of the receptor for the CTGF-2 polypeptide. The gene encoding the receptor can be identified by expression cloning. Briefly, polyadenylated RNA is prepared from a cell responsive to CTGF-2, and a cDNA library created from this RNA is divided into pools and used to transfect COS cells or other cells that are not responsive to CTGF-2. Transfected cells which are grown on glass slides are exposed to labeled CTGF-2. The CTGF-2 can be labeled by a variety of means including iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clone that encodes the putative receptor. As an alternative approach for receptor identification, labeled ligand can be photoaffinity linked with cell membrane or extract preparations that express the receptor molecule. Cross-linked material is resolved by PAGE and exposed to x-ray film. The labeled complex containing the CTGF-2-receptor can be excised, resolved into peptide fragments, and subjected to protein microsequencing. The amino acid sequence obtained from microsequencing would be used to design a set of generate oligonucleotide probes to screen a cDNA library to identify the gene encoding the putative receptor.

This invention also provides a method of screening compounds to identify those which bind to the CTGF-2 receptor and elicit a second messenger response (agonists) or do not elicit a second messenger response (antagonists). As an example, a mammalian cell or membrane preparation expressing the CTGF-2 receptor would be incubated with a labeled compound. The response of a known second messenger system following interaction of the compound and the CTGF-2 receptor is then measured. Such second messenger systems include but are not limited to, cAMP guanylate cyclase, ion channels or phosphoinositide hydrolysis.

Methods of Treatment

Stimulation of Angiogenesis

CTGF-2 stimulates angiogenesis. Thus, the CTGF-2 polynucleotides and polypeptides of the invention, described in detail above, are useful in the treatment of disorders in which stimulation of new blood vessel development would ameliorate the disorder. Such disorders include, but are not limited to, heart failure, angina, blood vessel (e.g. coronary artery) blockage and ischemia, inlcuding critical limb ischemia and refractory myocardial ischemia. CTGF-2 encoding polynucleotides can be delivered to individuals to using the gene therapy embodiments described above.

CTGF-2 polynucleotides or polypeptides, or agonists CTGF-2 of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. The polypeptide, polynucleotide, agonist, or antagonist of the present invention may also be employed to stimulate angiogenesis and limb regeneration, as discussed above.

Regeneration

CTGF-2 polynucleotides or polypeptides, or agonists CTGF-2 can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, CTGF-2 polynucleotides or polypeptides, or agonists CTGF-2, may increase regeneration of tissues difficult to heal. For example, increased tendon/ligament regeneration would quicken recovery time after damage. CTGF-2 polynucleotides or polypeptides, or agonists CTGF-2, of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by CTGF-2 polynucleotides or polypeptides, or agonists CTGF-2, to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the CTGF-2 polynucleotides or polypeptides, or agonists CTGF-2.

Inhibition of Angiogenesis

As detailed above, CTGF-2 stimulates angiogenesis. Thus, antagonists to CTGF-2 may be useful in the treatment disorders in which inhibition of angiogenesis would ameliorate the disorder. Such antagonists include, but are not limited to, antibodies, peptides, and other molecules that bind to CTGF-2, as well as ribozymes, antisense molecules, and triple helix forming oligonucleotides that interfere with the transcription and translation of the CTGF-2 genes, and are described in further detail, below. For example such antagonists may be used in accordance with the invention to treat cancers, such as solid tumors, including prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non-small cell lung cancer; colorectal cancer; advanced malignancies; blood born tumors (such as leukemias); benign tumors, for example hemangiomas, acoustic neuromas, neurofibromas, trachomas, and pyogenic granulomas; artheroscleric plaques; ocular angiogenic diseases, for example diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis.

Moreover, antagonists (i.e., peptides, antibodies, antisense, ribozyme, triple helix forming molecules and other CTGF-2 inhibitory molecules) that inhibit CTGF-2 activity are useful in inhibiting the angiogenesis of proliferative cells or tissues, either alone, as a protein fusion, or in combination with other polypeptides directly or indirectly, as described elsewhere herein. In a most preferred embodiment, such anti-angiogenic effect may be achieved indirectly, for example, through the inhibition of hematopoietic, tumor-specific cells, such as tumor-associated macrophages (See Joseph IB, et al. J Natl Cancer Inst, 90(21):1648–53 (1998), which is hereby incorporated by reference). Antibodies and peptides that bind and inhibit CTGF-2 may also result in inhibition of angiogenesis directly, or indirectly (See Witte L, et al., Cancer Metastasis Rev. 17(2):155–61 (1998), which is hereby incorporated by reference)).

The naturally occurring balance between endogenous stimulators and inhibitors of angiogenesis is one in which inhibitory influences predominate. Rastinejad et al., Cell 56:345–355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., Biotech. 9:630–634 (1991); Folkman et al., N. Engl. J. Med., 333:1757–1763 (1995); Auerbach et al., J. Microvasc. Res. 29:401–411 (1985); Folkman, Advances in Cancer Research, eds. Klein and Weinhouse, Academic Press, New York, pp. 175–203 (1985); Patz, Am. J. Opthalmol. 94:715–743 (1982); and Folkman et al., Science 221:719–725 (1983). In a number of pathological conditions, the process of angiogenesis contributes to the disease state. For example, significant data have accumulated which suggest that the growth of solid tumors is dependent on angiogenesis. Folkman and Klagsbrun, Science 235:442–447 (1987).

The present invention provides for treatment of diseases or disorders associated with neovascularization by administration of CTGF-2 antagonists (e.g., antibodies or peptides) of the present invention. Malignant and metastatic conditions which can be treated with the antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)). Thus, the present invention provides a method of treating an angiogenesis-related disease and/or disorder, comprising administering to an individual in need thereof a therapeutically effective amount of a CTGF-2 antagonist of the invention. For example CTGF-2 antagonists may be utilized in a variety of additional methods in order to therapeutically treat a cancer or tumor. Cancers which may be treated with CTGF-2 antagonists include, but are not limited to solid tumors, including prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non-small cell lung cancer; colorectal cancer; advanced malignancies; and blood born tumors such as leukemias. For example, polynucleotides, polypeptides, antagonists and/or agonists may be delivered topically, in order to treat cancers such as skin cancer, head and neck tumors, breast tumors, and Kaposi's sarcoma.

Within yet other aspects, CTGF-2 antagonists may be utilized to treat superficial forms of bladder cancer by, for example, intravesical administration. CTGF-2 antagonists may be delivered directly into the tumor, or near the tumor site, via injection or a catheter. Of course, as the artisan of ordinary skill will appreciate, the appropriate mode of administration will vary according to the cancer to be treated. Other modes of delivery are discussed herein.

For example, within one aspect of the present invention methods are provided for treating hypertrophic scars and keloids, comprising the step of administering a CTGF-2 antagonist of the invention to a hypertrophic scar or keloid. Within one embodiment of the present invention antagonists are directly injected into a hypertrophic scar or keloid, in order to prevent the progression of these lesions. This therapy is of particular value in the prophylactic treatment of conditions which are known to result in the development of hypertrophic scars and keloids (e.g., burns), and is preferably initiated after the proliferative phase has had time to progress (approximately 14 days after the initial injury), but before hypertrophic scar or keloid development.

The present invention also provides methods for treating neovascular diseases of the eye, including for example, corneal neovascularization, neovascular glaucoma, proliferative diabetic retinopathy, retrolental fibroplasia and macular degeneration.

Moreover, ocular disorders associated with neovascularization which can be treated with the polynucleotides and polypeptides of the present invention (including agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al, *Am. J. Ophthal.* 85:704–710 (1978) and Gartner et al, *Surv. Ophthal.* 22:291–312 (1978).

Thus, within one aspect of the present invention methods are provided for treating neovascular diseases of the eye such as corneal neovascularization (including corneal graft neovascularization), comprising the step of administering to a patient a therapeutically effective amount of a CTGF-2 antagonist to the cornea, such that the formation of blood vessels is inhibited. Briefly, the cornea is a tissue which normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates. A wide variety of disorders can result in corneal neovascularization, including for example, corneal infections (e.g., trachoma, herpes simplex keratitis, leishmaniasis and onchocerciasis), immunological processes (e.g., graft rejection and Stevens-Johnson's syndrome), alkali burns, trauma, inflammation (of any cause), toxic and nutritional deficiency states, and as a complication of wearing contact lenses.

Within particularly preferred embodiments of the invention, may be prepared for topical administration in saline (combined with any of the preservatives and antimicrobial agents commonly used in ocular preparations), and administered in eyedrop form. The solution or suspension may be prepared in its pure form and administered several times daily. Alternatively, anti-angiogenic compositions, prepared as described above, may also be administered directly to the cornea. Within preferred embodiments, the anti-angiogenic composition is prepared with a mucoadhesive polymer which binds to cornea. Within further embodiments, the anti-angiogenic factors or anti-angiogenic compositions may be utilized as an adjunct to conventional steroid therapy. Topical therapy may also be useful prophylactically in corneal lesions which are known to have a high probability of inducing an angiogenic response (such as chemical burns). In these instances the treatment, likely in combination with steroids, may be instituted immediately to help prevent subsequent complications.

Within other embodiments, the compounds described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2–3 times per year. A steroid could also be added to the injection solution to reduce inflammation resulting from the injection itself.

Within another aspect of the present invention, methods are provided for treating neovascular glaucoma, comprising the step of administering to a patient a therapeutically effective amount of a CTGF-2 antagonists to the eye, such that the formation of blood vessels is inhibited. In one embodiment, the compound may be administered topically to the eye in order to treat early forms of neovascular glaucoma. Within other embodiments, the compound may be implanted by injection into the region of the anterior chamber angle. Within other embodiments, the compound may also be placed in any location such that the compound is continuously released into the aqueous humor. Within another aspect of the present invention, methods are provided for treating proliferative diabetic retinopathy, comprising the step of administering to a patient a therapeutically effective amount of a polynucleotide, polypeptide, antagonist and/or agonist to the eyes, such that the formation of blood vessels is inhibited.

Within particularly preferred embodiments of the invention, proliferative diabetic retinopathy may be treated by injection into the aqueous humor or the vitreous, in order to increase the local concentration of the CTGF-2 antagonist in the retina. Preferably, this treatment should be initiated prior to the acquisition of severe disease requiring photocoagulation.

Within another aspect of the present invention, methods are provided for treating retrolental fibroplasia, comprising the step of administering to a patient a therapeutically effective amount of a CTGF-2 antagonist to the eye, such that the formation of blood vessels is inhibited. The compound may be administered topically, via intravitreous injection and/or via intraocular implants.

Additionally, disorders which can be treated with CTGF-2 antagonists include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, disorders and/or states, which can be treated with be treated with the the CTGF-2 antagonists include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vascluogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (*Rochele minalia quintosa*), ulcers (*Helicobacter pylori*), Bartonellosis and bacillary angiomatosis.

In one aspect of the birth control method, an amount of the compound sufficient to block embryo implantation is administered before or after intercourse and fertilization have occurred, thus providing an effective method of birth control, possibly a "morning after" method. CTGF-2 antagonists may also be used in controlling menstruation or administered as either a peritoneal lavage fluid or for peritoneal implantation in the treatment of endometriosis.

CTGF-2 antagonists of the present invention may be incorporated into surgical sutures in order to prevent stitch granulomas.

CTGF-2 antagonists may be utilized in a wide variety of surgical procedures. For example, within one aspect of the present invention a compositions (in the form of, for example, a spray or film) may be utilized to coat or spray an area prior to removal of a tumor, in order to isolate normal surrounding tissues from malignant tissue, and/or to prevent the spread of disease to surrounding tissues. Within other aspects of the present invention, compositions (e.g., in the form of a spray) may be delivered via endoscopic procedures in order to coat tumors, or inhibit angiogenesis in a desired locale. Within yet other aspects of the present invention, surgical meshes which have been coated with anti-angiogenic compositions of the present invention may be utilized in any procedure wherein a surgical mesh might be utilized. For example, within one embodiment of the invention a surgical mesh laden with an anti-angiogenic composition may be utilized during abdominal cancer resection surgery (e.g., subsequent to colon resection) in order to provide support to the structure, and to release an amount of the anti-angiogenic factor.

Within further aspects of the present invention, methods are provided for treating tumor excision sites, comprising administering a CTGF-2 antagonists to the resection margins of a tumor subsequent to excision, such that the local recurrence of cancer and the formation of new blood vessels at the site is inhibited. Within one embodiment of the invention, the anti-angiogenic compound is administered directly to the tumor excision site (e.g., applied by swabbing, brushing or otherwise coating the resection margins of the tumor with the anti-angiogenic compound). Alternatively, the anti-angiogenic compounds may be incorporated into known surgical pastes prior to administration. Within particularly preferred embodiments of the invention, the anti-angiogenic compounds are applied after hepatic resections for malignancy, and after neurosurgical operations.

Within one aspect of the present invention CTGF-2 antagonists may be administered to the resection margin of a wide variety of tumors, including for example, breast, colon, brain and hepatic tumors. For example, within one embodiment of the invention, anti-angiogenic compounds may be administered to the site of a neurological tumor subsequent to excision, such that the formation of new blood vessels at the site are inhibited.

The CTGF-2 antagonists of the present invention may also be administered along with other anti-angiogenic factors. Representative examples of other anti-angiogenic factors include: Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., Cancer Res. 51:22–26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321–17326, 1992); Chymostatin (Tomkinson et al., Biochem J. 286:475–480, 1992); Cyclodextrin Tetradecasulfate; Eponemycin; Camptothecin; Fumagillin (Ingber et al., Nature 348:555–557, 1990); Gold Sodium Thiomalate ("GST"; Matsubara and Ziff, J. Clin. Invest. 79:1440–1446, 1987); anticollagenase-serum; alpha2-antiplasmin (Holmes et al., J. Biol. Chem. 262(4):1659–1664, 1987); Bisantrene (National Cancer Institute); Lobenzarit disodium (N-(2)-carboxyphenyl-4-chloroanthronilic acid disodium or "CCA"; Takeuchi et al., Agents Actions 36:312–316, 1992); Thalidomide; Angostatic steroid; AGM-1470; carboxynaminolmidazole; and metalloproteinase inhibitors such as BB94.

Antagonists

The present invention is also directed to antagonists molecules of the polypeptides of the present invention, and their use in reducing or eliminating the function of CTGF-2.

An example of an antagonist is an antibody or in some cases, an oligonucleotide, which binds to the CTGF-2 polypeptide. Alternatively, antagonists include closely related proteins that have lost biological function and thereby prevent the action of CTGF-2 since receptor sites are occupied.

Antisense technology may be employed to decrease the level of in vivo circulation of CTGF-2. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of CTGF-2. The antisense RNA oligonucleotide hybridizes to the mRNA in vivo and blocks translation of the mRNA molecule into CTGF-2 (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of CTGF-2.

Another example of an antagonist is a small molecule which binds to the CTGF-2 receptors such that normal biological activity is prevented. Examples of small molecules include but are not limited to small peptides or peptide-like molecules.

The antagonists may be employed to prevent scar formation due to excess proliferation of connective tissues and to prevent CTGF-2 dependent tumor growth. The antagonists may be employed in a composition with a pharmaceutically acceptable carrier, e.g., as hereinabove described.

Formulations and Administration

The polypeptides and antagonists and agonists of the present invention may be employed in combination with a suitable pharmaceutical carrier. Such compositions comprise a therapeutically effective amount of the polypeptide, agonist or antagonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides, agonists and antagonists of the present invention may be employed in conjunction with other therapeutic compounds.

The pharmaceutical compositions may be administered in a convenient manner such as by the topical, intravenous, intraperitoneal, intramuscular, subcutaneous, intranasal or intradermal routes. CTGF-2 is administered in an amount which is effective for treating and/or prophylaxis of the specific indication. In general, CTGF-2 will be administered in an amount of at least about 10 Fg/kg body weight and in most cases CTGF-2 will be administered in an amount not in excess of about 8 mg/Kg body weight per day. In most cases, the dosage is from about 10 Fg/kg to about 1 mg/kg body weight daily, taking into account the routes of administration, symptoms, etc.

The polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., Biotechniques, Vol. 7, No. 9, 980–990 (1989), or any other promoter (e.g., cellular promoters such as eukaryotic cellular promoters including, but not limited to, the histone, pol III, and â-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the â-actin promoter; and human growth hormone promoters. The promoter also may be the native promoter which controls the gene encoding the polypeptide. The retroviral plasmid vector is employed to transduce packaging cell lines to form producer cell lines. Examples of packaging cells which may be transfected include, but are not limited to, the PE501, PA317, ø-2, ø-AM, PA12, T19-14X, VT-19-17-H2, øCRE, øCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the gene of the present invention as a diagnostic. Detection of a mutated form of the gene will allow a diagnosis of a disease or a susceptibility to a disease which results from underexpression of CTGF-2.

Individuals carrying mutations in the gene of the present invention may be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding CTGF-2 can be used to identify and analyze mutations. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of the polypeptide of the present invention in various tissues since an over-expression of the proteins compared to normal control tissue samples can detect the presence of disorders of the host. Assays used to detect levels of the polypeptide of the present invention in a sample derived from a host are well-known to those of skill in the art and include radioimmunoassays, competitive-binding assays, Western Blot analysis and preferably an ELISA assay. An ELISA assay initially comprises preparing an antibody specific to the CTGF-2 antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attached to the polypeptide of the present invention attached to the polystyrene dish. All unbound monoclonal antibody is washed out with buffer. The reporter antibody linked to horseradish peroxidase is now placed in the dish resulting in binding of the reporter antibody to any monoclonal antibody bound to the polypeptide of the present invention. Unattached reporter antibody is then washed out. Peroxidase substrates are then added to the dish and the amount of color developed in a given time period is a measurement of the amount of the polypeptide of the present invention present in a given volume of patient sample when compared against a standard curve.

A competition assay may be employed wherein antibodies specific to the polypeptide of the present invention are attached to a solid support and labeled CTGF-2 and a sample derived from the host are passed over the solid support and the amount of label detected attached to the solid support can be correlated to a quantity of the polypeptide of the present invention in the sample.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA having at least 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µig of DNA are digested with 20 to 250 units of enzyme in a larger volume. Appropriate buffers and substrate amounts for particular restriction enzymes are specified by the manufacturer. Incubation times of about 1 hour at 37EC are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Cloning and Expression of CTGF-2 in a Baculovirus Expression System

The DNA sequence encoding the full length CTGF-2 protein, ATCC accession no. 75804, was amplified using PCR oligonucleotide primers corresponding to the 5' and 3' sequences of the gene:

The 5' primer has the sequence CGCGGGATCCTGCGC-GACACAATGAGCT (SEQ ID NO:3) and contains a BamHI restriction enzyme site (in bold) followed by 18 nucleotides resembling an efficient signal for the initiation of translation in eukaryotic cells (J. Mol. Biol. 1987, 196, 947–950, Kozak, M.). The initiation codon for translation "ATG" is underlined.

The 3' primer has the sequence CGCGGGTACCAGG-TAGCATTTAGTCCCTAA (SEQ ID NO:8) and contains the cleavage site for the restriction endonuclease Asp781 and 20 nucleotides complementary to the 3' non-translated sequence of the CTGF-2 gene. The amplified sequences were isolated from a 1% agarose gel using a commercially available kit ("Geneclean", BIO 101 Inc., La Jolla, Calif.). The fragment was then digested with the endonucleases BamHI and Asp781 and then purified by isolation on a 1% agarose gel. This fragment is designated F2.

The vector pRG1 (modification of pVL941 vector, discussed below) is used for the expression of the CTGF-2 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases BamHI and Asp781. The polyadenylation site of the simian virus (SV)40 is used for efficient polyadenylation. For an easy selection of recombinant viruses the beta-galactosidase gene from E.coli is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid was digested with the restriction enzymes BamHI and Asp781 and then dephosphorylated using calf intestinal phosphatase by procedures known in the art. The DNA was then isolated from a 1% agarose gel. This vector DNA is designated V2.

Fragment F2 and the dephosphorylated plasmid V2 were ligated with T4 DNA ligase. E.coli HB101 cells were then transformed and bacteria identified that contained the plasmid (pBacCTGF-2) with the CTGF-2 gene using the enzymes BamHI and Asp781. The sequence of the cloned fragment was confirmed by DNA sequencing.

5 µg of the plasmid pBacCTGF-2 were cotransfected with 1.0 µg of a commercially available linearized baculovirus ("BaculoGold baculovirus DNA", Pharmingen, San Diego, Calif.) using the lipofection method (Felgner et al. Proc. Natl. Acad. Sci. USA, 84:7413–7417 (1987)).

1 µg of BaculoGold virus DNA and 5 µg of the plasmid pBacCTGF-2 were mixed in a sterile well of a microtiter plate containing 50 µl of serum free Grace's medium (Life Technologies Inc., Gaithersburg, Md.). Afterwards 10 µl Lipofectin plus 90 µl Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace' medium without serum. The plate was rocked back and forth to mix the newly added solution. The plate was then incubated for 5 hours at 27EC. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution of the viruses was added to the cells, blue stained plaques were picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculoviruses was used to insect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-CTGF-2 at a multiplicity of infection (MOI) of 2. Six hours later the medium was removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) were added. The cells were further incubated for 16 hours before they were harvested by centrifugation and the labelled proteins visualized by SDS-PAGE and autoradiography.

EXAMPLE 2

Expression of Recombinant CTGF-2 in COS Cells

The expression of plasmid, CTGF-2 HA is derived from a vector pcDNAI/Amp (Invitrogen) containing: 1) SV40 origin of replication, 2) ampicillin resistance gene, 3) E.coli* replication origin, 4) CMV promoter followed by a polylinker region, a SV40 intron and polyadenylation site. A DNA fragment encoding the entire CTGF-2 precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lemer, 1984, Cell 37, 767). The infusion of HA tag to our target protein allows easy detection of the recombinant protein with an antibody that recognizes the HA epitope.

The plasmid construction strategy is described as follows:

The DNA sequence encoding for CTGF-2, ATCC accession no. 75804, was constructed by PCR on the full-length clone using two primers: the 5' primer 5' AAAGGATCCA-CAATGAGCTCCCGAATC 3' (SEQ ID NO:4) contains a Bam HI site followed by 18 nucleotides of CTGF-2 coding sequence starting from the −3 position relative to the initiation codon; the 3' sequence 5' CGCTCTAGATTAAGCG-TAGTCTGGGACGTCGTATGGGTATTG-GAACAGCCTGTAG AAG 5' (SEQ ID NO:5) contains complementary sequences to an Xba I site, translation stop codon, HA tag and the last 19 nucleotides of the CTGF-2 coding sequence (not including the stop codon). Therefore, the PCR product contains a Bam HI site, CTGF-2 coding sequence followed by an HA tag fused in frame, a translation termination stop codon next to the HA tag, and an Xba I site. The PCR amplified DNA fragment and the vector, pcDNAI/Amp, were digested with Bam HI and Xba I restriction enzymes and ligated. The ligation mixture transformed into E. coli strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant CTGF-2, COS cells were transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the CTGF-2 HA protein was detected by radiolabelling and immunoprecipitation method. (E. Harlow, D. Lane, Antibodies: A Laboratory Manual, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media were precipitated with a HA specific monoclonal antibody. Proteins precipitated were analyzed on 15% SDS-PAGE gels.

EXAMPLE 3

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

EXAMPLE 4

Effect of CTGF-2 on Cord Formation in Angiogenesis

A step in angiogenesis is cord formation, marked by differentiation of endothelial cells. This bioassay measures the ability of microvascular endothelial cells to form capillary-like structures (hollow structures) when cultured in vitro.

CADMEC (microvascular endothelial cells) are purchased from Cell Applications, Inc. as proliferating (passage 2) cells and are cultured in Cell Applications' CADMEC Growth Medium and used at passage 5. For the in vitro angiogenesis assay, the wells of a 48-well cell culture plate are coated with Cell Applications' Attachment Factor Medium (200 microliter/well) for 30 min. at 37° C. CADMEC are seeded onto the coated wells at 7,500 cells/well and cultured overnight in Growth Medium. The Growth Medium is then replaced with 300 micrograms Cell Applications' Chord Formation Medium containing control buffer or CTGF-2 (0.1 to 100 ng/ml) and the cells are cultured for an additional 48 hr. The numbers and lengths of the capillary-like chords are quantitated through use of the Boeckeler VIA-170 video image analyzer. All assays are done intriplicate.

Commercial (R&D) VEGF (50 ng/ml) is used as a positive control. beta-esteradiol (1 ng/ml) is used as a negative control. The appropriate buffer (without protein) is also utilized as a control.

The studies described in this example test the activity in CTGF-2 protein. However, one skilled in the art could easily modify the exemplified studies to test the activity of CTGF-2 polynucleotides (e.g., gene therapy), agonists, and/or antagonists of CTGF-2.

EXAMPLE 5

Angiogenic Effect on Chick Chorioaollantoic Membrane

Chick chorioallantoic membrane (CAM) is a well-established system to examine angiogenesis. Blood vessel formation on CAM is easily visible and quantifiable. The ability of CTGF-2 to stimulate angiogenesis in CAM can be examined.

Fertilized eggs of the White Leghorn chick (*Gallus gallus*) and the Japanese quail (*Coturnix coturnix*) are incubated at 37.8° C. and 80% humidity. Differentiated CAM of 16-day-old chick and 13-day-old quail embryos is studied with the following methods.

On Day 4 of development, a window is made into the egg shell of chick eggs. The embryos are checked for normal development and the eggs sealed with cellotape. They are further incubated until Day 13. Thermanox coverslips (Nunc, Naperville, Ill.) are cut into disks of about 5 mm in diameter. Sterile and salt-free growth factors, and the protein to be tested, are dissolved in distilled water and about 3.3 mg/5 ml are pipetted on the disks. After air-drying, the inverted disks are applied on CAM. After 3 days, the specimens are fixed in 3% glutaraldehyde and 2% formaldehyde and rinsed in 0.12 M sodium cacodylate buffer. They are photographed with a stereo microscope [Wild M8] and embedded for semi- and ultrathin sectioning as described above. Controls are performed with carrier disks alone.

The studies described in this example test the activity in CTGF-2 protein. However, one skilled in the art could easily modify the exemplified studies to test the activity of CTGF-2 polynucleotides (e.g., gene therapy), agonists, and/or antagonists of CTGF-2.

EXAMPLE 6

Angiogenesis Assay Using a Matrigel Implant in Mouse

In order to establish an in vivo model for angiogenesis to test CTGF-2 protein activities, mice and rats are implanted subcutaneously with methylcellulose disks containing either 20 mg of BSA (negative control), 1 mg of CTGF-2 or 0.5 mg of VEGF-1 (positive control). The negative control disks should contain little vascularization, while the positive control disks should show signs of vessel formation.

The studies described in this example test the activity in CTGF-2 protein. However, one skilled in the art could easily modify the exemplified studies to test the activity of CTGF-2 polynucleotides (e.g., gene therapy), agonists, and/or antagonists of CTGF-2.

EXAMPLE 7

Rescue of Ischemia in Rabbit Lower Limb Model

To study the in vivo effects of CTGF-2 on ischemia, a rabbit hindlimb ischemia model is created by surgical removal of one femoral arteries as described previously (Takeshita, S. et al., Am J. Pathol 147:1649–1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshita, S. et al., Am J. Pathol 147:1649–1660 (1995)). An interval of 10 days is allowed for post-operative recovery of rabbits and development of endogenous collateral vessels. At 10 day post-operatively (day 0), after performing a baseline angiogram, the internal iliac artery of the ischemic limb is transfected with 500 mg naked CTGF-2 expression plasmid by arterial gene transfer technology using a hydrogel-coated balloon catheter as described (Riessen, R. et al., Hum Gene Ther. 4:749–758 (1993); Leclerc, G. et al., J. Clin. Invest. 90: 936–944 (1992)). When CTGF-2 is used in the treatment, a single bolus of 500 mg CTGF-2 protein or control is delivered into the internal iliac artery of the ischemic limb over a period of 1 min. through an infusion catheter. On day 30, various parameters are measured in these rabbits: (a) BP ratio—The blood pressure ratio of systolic pressure of the ischemic limb to that of normal limb; (b) Blood Flow and Flow Reserve—Resting FL: the blood flow during undilated condition and Max FL: the blood flow during fully dilated condition (also an indirect measure of the blood vessel amount) and Flow Reserve is reflected by the ratio of max FL: resting FL; (c) Angiographic Score—This is measured by the angiogram of collateral vessels. A score is determined by the percentage of circles in an overlaying grid that with crossing opacified arteries divided by the total number m the rabbit thigh; (d) Capillary density—The number of collateral capillaries determined in light microscopic sections taken from hindlimbs.

The studies described in this example test the activity in CTGF-2 protein. However, one skilled in the art could easily modify the exemplified studies to test the activity of CTGF-2 polynucleotides (e.g., gene therapy), agonists, and/or antagonists of CTGF-2.

EXAMPLE 8

Rat Ischemic Skin Flap Model

The evaluation parameters include skin blood flow, skin temperature, and factor VIII immunohistochemistry or endothelial alkaline phosphatase reaction. CTGF-2 expression, during the skin ischemia, is studied using in situ hybridization.

The study in this model is divided into three parts as follows:

Ischemic skin

Ischemic skin wounds

Normal wounds

The experimental protocol includes:

Raising a 3×4 cm, single pedicle full-thickness random skin flap (myocutaneous flap over the lower back of the animal).

An excisional wounding (4–6 mm in diameter) in the ischemic skin (skin-flap).

Topical treatment with CTGF-2 of the excisional wounds (day 0, 1, 2, 3, 4 post-wounding) at the following various dosage ranges: 1 mg to 100 mg.

Harvesting the wound tissues at day 3, 5, 7, 10, 14 and 21 post-wounding for histological, immunohistochemical, and in situ studies.

The studies described in this example test the activity in CTGF-2 protein. However, one skilled in the art could easily modify the exemplified studies to test the activity of CTGF-2 polynucleotides (e.g., gene therapy), agonists, and/or antagonists of CTGF-2.

EXAMPLE 9

Peripheral Arterial Disease Model

Angiogenic therapy using CTGF-2 is a novel therapeutic strategy to obtain restoration of blood flow around the ischemia in case of peripheral arterial diseases. The experimental protocol includes:

One side of the femoral artery is ligated to create ischemic muscle of the hindlimb, the other side of hindlimb serves as a control.

CTGF-2 protein, in a dosage range of 20 mg–500 mg, is delivered intravenously and/or intramuscularly 3 times (perhaps more) per week for 2–3 weeks.

The ischemic muscle tissue is collected after ligation of the femoral artery at 1, 2, and 3 weeks for the analysis of CTGF-2 expression and histology. Biopsy is also performed on the other side of normal muscle of the contralateral hindlimb.

The studies described in this example test the activity in CTGF-2 protein. However, one skilled in the art could easily modify the exemplified studies to test the activity of CTGF-2 polynucleotides (e.g., gene therapy), agonists, and/or antagonists of CTGF-2.

EXAMPLE 10

Ischemic Myocardial Disease Model

CTGF-2 is evaluated as a potent mitogen capable of stimulating the development of collateral vessels, and restructuring new vessels after coronary artery occlusion. Alteration of CTGF-2 expression is investigated in situ. The experimental protocol includes:

The heart is exposed through a left-side thoracotomy in the rat. Immediately, the left coronary artery is occluded with a thin suture (6-0) and the thorax is closed.

CTGF-2 protein, in a dosage range of 20 mg–500 mg, is delivered intravenously and/or intramuscularly 3 times (perhaps more) per week for 2–4 weeks.

Thirty days after the surgery, the heart is removed and cross-sectioned for morphometric and in situ analyzes.

The studies described in this example test the activity in CTGF-2 protein. However, one skilled in the art could easily modify the exemplified studies to test the activity of CTGF-2 polynucleotides (e.g., gene therapy), agonists, and/or antagonists of CTGF-2.

EXAMPLE 11

Rat Corneal Wound Healing Model

This animal model shows the effect of CTGF-2 on neovascularization. The experimental protocol includes:

Making a 1–1.5 mm long incision from the center of cornea into the stromal layer.

Inserting a spatula below the lip of the incision facing the outer corner of the eye.

Making a pocket (its base is 1–1.5 mm form the edge of the eye).

Positioning a pellet, containing 50 ng–5 ug of CTGF-2, within the pocket.

CTGF-2 treatment can also be applied topically to the corneal wounds in a dosage range of 20 mg–500 mg (daily treatment for five days).

The studies described in this example test the activity in CTGF-2 protein. However, one skilled in the art could easily modify the exemplified studies to test the activity of CTGF-2 polynucleotides (e.g., gene therapy), agonists, and/or antagonists of CTGF-2.

EXAMPLE 12

Therapeutic Angiogenesis By Adenoviral-Mediated CTGF-2 Gene Transfer

Connective tissue growth factor 2 (CTGF-2) is a secreted, cystein-rich heparin-binding protein that is associated with extracellular matrix and cell surface. In this Example the angiogenic effect of the human CTGF-2 was evaluated in comparison with the vascular endothelial growth factor ($VEGF_{165}$) in an adenoviral context after intramuscular administration (IM) in the rabbit ischemic hindlimb model.

Briefly, three randomized groups of New Zealand White rabbits received IM injections of $5 \times 10^8$ infectious units (i.u.) of an adenovirus carrying either the CTGF-2 gene (Ad-CTGF-2), the $VEGF_{165}$ gene (Ad-$VEGF_{165}$) or no transgene (Ad-Null), ten days after femoral artery excision in one limb. Perfusion of the ischemic limb was evaluated before adenoviral treatment (day 10) and 30 days post-injection (day 40). Angiographic, hemodynamic and histologic parameters indicated that animals in the Ad-CTGF-2 group had a significantly better perfusion than in the Ad-Null group. Interestingly, this improvement exceeded that achieved with Ad-$VEGF_{165}$.

These results show that CTGF-2 gene transfer demonstrates a stronger stimulus for limb revascularization compared to $VEGF_{165}$, thereby promoting a greater improvement in tissue perfusion in the ischemic limb. These findings show that CTGF-2 is useful for treating of severe peripheral ischemic diseases.

Despite substantial advances in prevention and treatment of ischemic diseases, an increasing number of patients with advanced peripheral ischemia remain untreatable by angioplasty or surgical revascularization. Therefore, alternative treatments for these patients are compelling. Therapeutic angiogenesis, i.e., the clinical use of growth factors to enhance revascularization in ischemic tissue, may be a promising strategy in this setting.

Among the numerous angiogenic growth factors that have been tested in preclinical studies, vascular endothelial growth factor (VEGF)[1-5], and fibroblast growth factor (FGF) families[6,7] are the most widely studied. They can be considered as the first line of therapeutic candidates that have been used in clinical setting[8,9,10]. Despite some promising results, the early clinical trials indicate that the optimal angiogenic factor has not yet been identified, stimulating the search for new therapeutic candidates.

Connective tissue growth factor 2 (also named cyr61) is a member of the CCN family which comprises six distinct proteins (Fisp12/CTGF, Cyr61, Nov, Elm-1, Cop-1/Wisp2, and Wisp3) involved in cell growth and differentiation[11]. CTGF-2 is encoded by a growth factor-inducible immediate-early gene that is transcriptionally activated by serum and growth factors (bFGF, PDGF and TGFβ)[12-14]. CTGF-2 is a 42-kDa secreted, cysteine-rich heparin-binding protein that is associated with extracellular matrix and cell surface[11,15,16]. Recombinant CTGF-2 protein mediates adhesion of vascular endothelial cells, fibroblasts and lung epithelial cells[17-19], stimulates migration of fibroblasts and vascular endothelial cells[20] and synergizes bFGF-induced DNA synthesis in both endothelial cells and fibroblasts[17,21]. The potential interest of CTGF-2 in vivo is poorly investigated since only one study performed in a rat corneal micropocket angiogenesis model demonstrated the angiogenic effect of CTGF-2[20].

Therefore, the purpose of the present study was to examine the angiogenic effects of adenoviral-mediated gene transfer of human CTGF-2 in the rabbit ischemic hindlimb models[22], in comparison with those observed with $VEGF_{165}$. Perfusion of the ischemic limb was evaluated before treatment and 30 days after direct intramuscular injection of an adenovirus carrying either CTGF-2 gene (Ad-CTGF-2), $VEGF_{165}$ gene (Ad-$VEGF_{165}$) or no transgene (Ad-Null). Results demonstrated that Ad-CTGF-2 gene transfer promotes a significant improvement of tissue perfusion in the ischemic limb. CTGF-2 appeared more prone to stimulate limb revascularization in comparison with $VEGF_{165}$, indicating that CTGF-2 represents a promising candidate for therapeutic gene-based angiogenesis for promote, for example, perfusion in the ischemic limb in severe peripheral ischemic diseases.

Methods:

Adenoviral Vectors

The recombinant E1/E3-deleted adenoviral vectors containing the human CTGF-2 cDNA (cDNA clone ID HLFBE49; Ad-CTGF-2) or the human cDNA sequence encoding the $VEGF_{165}$ protein (RT-PCR from HUVEC; Ad-$VEGF_{165}$) under the control of the Cytornegalovirus promoter were obtained by homologous recombination[23]. Virus propagation, purification and titration of infectious units (i.u.) by indirect immunofluorescence of the viral DNA binding were carried out as described previously[24].

More specifically, the HLFBE49 cDNA clone contained a BamHI restriction enzyme site at the 5' and 3' sequences. After digestion, the Bam/Bam fragment was isolated from a 1% agarose gel using a commercially avalaible kit ("Qiaquick", Qiagen, Courtaboeuf, France) and cloned in the Bam HI site of a pBluescript phagemid vector (Stratagene, La Jolla, Calif.). Ligation mixture was transformed into DH5α strain. Plasmid DNA was isolated from transformnants and examined by restriction analysis for the presence of the correct fragment. The candidate clone was sequenced, and then, digested with Eco RI/Xba I restriction enzymes for the ligation with the transfer vector (named pTG13387). This transfer vector contains the Ad5 1–458 region followed by the CMV enhancer/promoter and a a chimeric intron generated combining the splice donor from the human β-globin intron 1 and the splice acceptor from the IgG intervening sequence obtained from pCI plasmid (Promega, Charbonnieres, France). The recognition sites for the restriction endonucleases XbaI and EcoRI was inserted upstream of the bovine growth hormone polyadenylation site followed by the Ad5 3511–5788 and 3512–5788 regions. This vector contains the ampicillin resistance gene.

The E1/E3-deleted adenoviral vector containing the gene encoding CTGF-2 (named AdTG14550) was obtained by homologous recombination in 293 cells[23], between the CTGF-2 transfer vector (named pTG14488) and the genomic ClaI DNA fragment isolated from the H5d1324 virus.

Virus propagation, purification and titration of infectious units (iu) by indirect immunofluorescence of the viral DNA binding protein were carried out as described previously[24]. Purified virus was stored in viral storage buffer (1 M sucrose, 10 mM Tris-HCl [pH=8.5], 1 mM $MgCl_2$, 150 mM NaCl, 0.005% [vol/vol] Tween 80).

In vitro Angiogenesis Assay

Human dermal microvascular endothelial cells (HDMEC) were purchased from PromoCell (Heidelberg, Germany). Cells were grown and maintained in Endothelial Cell Growth Medium (ECGM) supplemented with 5% Fetal Calf Serum (FCS), 10 ng/ml Epidermal Growth Factor and 0.4% Endothelial Cell Growth Supplement. Cells were infected with recombinant adenovirus at a multiplicity of infection of 50 for 12 hours and cell supernatants were then collected. For the migration assay, $1\times10^5$ cells were added to the upper side of 5 μm pore size Transwell migration chambers (Costar) in ECGM containing 5% FCS. Adenoviral-infected HDMEC supernatants were added in the lower compartment and cell migration was allowed to proceed at 37° C. for 3.5 hours. Cells that migrated to the underside were stained with 0.5% crystal violet in 70% methanol followed by a brief rinse in PBS and counted on nine randomly selected microscopic fields (magnification×20) for each condition.

Rabbit Model

The animal experiments were performed in accordance with *Guiding Principles in the Care and Use of Animals* approved by the American Physiological Society.

Male New Zealand White rabbits (3–3.25 kg) were anesthetized with a mixture of ketamine (50 mg/kg) and acepromazine (0.8 mg/kg) after premedication with xylazine (2 mg/kg), all injected intramuscularly. The surgical excision of the femoral artery was performed as described previously[1]. Postoperation, prophylactic antibiotics (15 mg/kg sulfamethoxazole and 3 mg/kg trimethoprim) were administered subcutaneously and analgesia (1 g paracetamol) was added in the drinking water.

Intramuscular Gene Transfer

Animals (n=24) were randomly divided into 3 groups. An interval of 10 days was permitted for postoperative recovery (day 10). Rabbits were injected either with $5.10^8$ i.u. of Ad-Null, Ad-$VEGF_{165}$ or Ad-CTGF-2 in five muscular sites [medial large (×2), adductor (×2), semimembranous], after completion of baseline measurements (angiography, Doppler-derived flow).

Angiography and Doppler-derived Blood Flow at Rest and After Papaverine Infusion In each animal, angiography and blood flow measurement were performed before adenoviral injection (day 10) and 30 days after injection (day 40) as described previously[1]. A 4-French infusion catheter introduced through the common carotid artery was positioned to the aortoiliac bifurcation. After intra-arterial injection of nitroglycerin (0.25 mg), a bolus of contrast media was injected and serial images of the aortoiliac bifurcation were recorded to obtain angiograms. Subsequently, a 0.014-in Doppler guide wire (Cardiometrics, Mountain view, Calif.) was positioned in the proximal segment of either the internal iliac artery supplying the ischemic limb or the common iliac artery supplying the non-ischemic limb. Average peak velocities (APV) were recorded at rest and after bolus injection of 2 mg of papaverine (maximum APV). Angiographic luminal diameter of the internal iliac artery in the ischemic limb and of the common iliac artery in the normal limb were determined with an automated edge-detection system. The luminal diameter was measured at the site of the Doppler wire position.

Vascular Density

A morphometric angiographic analysis of collateral vessel development in the ischemic limb was performed using the angiograms recorded at day 10 and day 40. A grid overlay composed of 5-$mm^2$ squares was placed over the angiogram at the level of the medial thigh area, positioned always at the same place considering anatomic references. The number of contrast-opacified arteries crossing over rows in two sides were counted in a single blind fashion. This angiographic score reflects vascular density in the medial thigh.

Capillary Density

At the time of sacrifice, tissue samples were harvested from the adductor and semimembranous muscles of the ischemic limb. Muscles were frozen in iced-isopentane and stored at −80° C. Transverse tissue sections (7 μm) were stained for alkaline phosphatase with an indoxyl-tetrazolium method[25] to detect capillary endothelial cells. A total of 20 randomly selected microscopic fields for each muscle were examined under a 10× objective to determine the mean number of capillaries and myofibers to calculate the capillary-to-muscle fiber ratio.

Statistical Analysis

All results are expressed as means±SEM. For parametric data, statistical significance was evaluated using unpaired or paired Students t-test for comparison between two means and two-way analysis of variance (ANOVA) followed by Fishers test for more than two mean values. Mann-Withney rank sum test was used for comparison of non parametric data if the interaction exists with analysis of variance (Kriskall-Wallis). A value of P<0.05 was interpreted to denote statistical significance.

EXAMPLE 12 RESULTS

In vitro Studies

As shown in FIG. 2, Ad-CTGF-2 and Ad-VEGF$_{165}$-infected cell supernatants enhanced significantly the migration of HDMEC in comparison with Ad-Null (P<0.05), validating adenoviral-mediated gene expression and angiogenic activities of the gene product. The stimulation of cell migration by Ad-VEGF$_{165}$ or by Ad-CTGF-2 was similar.

In vivo Studies

Resting and Stimulated Doppler-derived Blood Flows

In the ischemic limb, rest blood flows or maximal blood flows did not differ significantly among groups at day 10. At day 40, however, Ad-VEGF$_{165}$ and Ad-CTGF-2-treated animals had a significant increase in blood flows compared with day 10 both at rest (FIG.3A; Ad-VEGF$_{165}$: +77%; P<0.01 and Ad-CTGF-2: +125.3%; P<0.01) and after papaverine infusion (FIG.3B; Ad-VEGF$_{165}$: +78.9%; P<0.01 and Ad-CTGF-2: +151.5%; P<0.01). Rest blood flow as well as maximum blood flow were significantly improved in Ad-CTGF-2 animals compared with Ad-Null group (rest flow: P<0.05 and maximum flow: P<0.05). A trend toward greater blood flows appeared in Ad-CTGF-2 in comparison with Ad-VEGF$_{165}$-treated rabbits, but the difference was not statistically significant (NS).

In the non ischemic limb, baseline and hyperemic blood flows determined at day 10 were not different from those obtained at day 40 either in each group or among groups (data not shown). When ischemic and non-ischemic limb blood flows were compared at day 10, rest and stimulated blood flows were significantly higher in the normal limb whereas at day 40, rest blood flow was restored in Ad-VEGF$_{165}$ and Ad-CTGF-2 groups (Ad-VEGF$_{165}$ :13.1±1.4 versus 16.4±2.5 ml/min, NS; Ad-CTGF-2: 18.6±2.8 versus 19.6±4.5 ml/min, NS) but remained altered in Ad-Null-treated rabbits (Ad-Null: 10.8±1.7 versus 17.9±2.3 ml/min, P<0.01). Moreover, maximum blood flow was also restored in Ad-CTGF-2 group (34.2±5.5 versus 50.8±10.7 ml/min, NS) whereas it was not in Ad-VEGF$_{165}$ or in Ad-Null groups (P<0.05).

Vessel Diameter

In the ischemic limb (FIG. 4 ), a significant increase in angiographic luminal diameter of the internal iliac artery was observed during the 30 days of the follow-up period in Ad-VEGF$_{165}$ (P<0.001) and Ad-CTGF-2-treated animals (P<0.001) but not in Ad-Null group, reflecting the expansive remodeling of the artery supplying the ischemic limb in response to the chronic increase of blood flow. At day 40 the diameter was significantly higher in Ad-CTGF-2-treated rabbits than in Ad-Null group (P<0.05).

Angiographic luminal diameters of the common iliac artery showed no significant modification in diameter at day 10 and day 40 between the three groups (data not shown).

Vascular Density

Representative angiograms of rabbit ischemic hindlimb showed that collateral vessel development during the 30 days of the follow-up period was more marked in the Ad-VEGF$_{165}$ and the Ad-CTGF-2-treated groups, over control groups (FIG. 5). The quantitative analysis of collateral blood vessel development in rabbit hindlimb is summarized in FIG. 6. Angiographic scores did not differ significantly among groups before treatment at day 10. An increase in vascular density was measured in each group from day 10 to day 40 (Ad-Null: +26.3%; P<0.01; Ad-VEGF$_{165}$: +76.4%; P<0.0001 and Ad-CTGF-2: +100.7%; P<0.001). At day 40, vascular densities were significantly higher in both treated groups compared with control animals (P<0.0001) as suggested on angiograms. Interestingly, the angiographic score in CTGF-2-treated animals exceeded that of the VEGF$_{165}$-treated group (P<0.01), indicating a marked effect of CTGF-2 on arteriogenesis.

Capillary Density

In the adductor muscle (FIG.7A), capillary density as capillary-to-myocyte ratio was increased in the Ad-CTGF-2 group compared with Ad-Null (P<0.01) and Ad-VEGF$_{165}$-treated animals (P<0.001) whereas there was no difference between these two last groups. In the semimembranous muscle (FIG.7B), the capillary density was significantly higher in Ad-VEGF$_{165}$ compared with Ad-Null group (P<0.05). An increase was also observed in the Ad-CTGF-2 group in comparison to the Ad-Null group but the level of significance was not reached.

These results demonstrate in vivo, the angiogenic potency of human CTGF-2 adenoviral-mediated gene transfer. Indeed, experiments performed on rabbit ischemic hindlimb provided evidence that Ad-CTGF-2 improves limb perfusion, as suggested by the augmentation of angiographically visible collateral vessels, increased capillary density, and consequent hemodynamic improvement.

The choice of VEGF$_{165}$ as a reference has been suggested by the extensive literature demonstrating its potent angiogenic effect. Nevertheless, adenoviral-mediated gene transfer of VEGF$_{165}$ has never been used in the rabbit ischemic hindlimb model.

In this study, data obtained in Ad-VEGF$_{165}$-treated animals are in good general agreement with previous findings demonstrating that VEGF administered as a recombinant protein or as naked DNA increased limb perfusion[22,26,27]. In fact, we showed an increase in rest as well as maximal blood flows, angiographic score and capillary density in the adductor muscle.

In animals treated with Ad-CTGF-2, a marked improvement of the blood flows in the ischemic limb was obtained and measured. This improvement in hemodynamic status seems related to the stimulation of angiogenesis and arteriogenesis as revealed by increased capillary density in the semimembranous muscle as well as increased angiographic score in Ad-CTGF-2-treated animals. Although angiogenesis (capillary sprouting) may deliver some relief to the underperfused territory, only true collateral arteries, resulting from in situ proliferation of preexisting arteriolar connections, are capable of providing large enough amounts of blood flow to the ischemic area to reestablish flow to the more distal arteries in the leg[28]. This enhanced arteriogenesis contributed, at least partly, to the increase in blood flows between day 10 and day 40 at rest as well as after papaverine-mediated arteriolar vasodilatation. Interestingly, CTGF-2 appears to be more efficient than $VEGF_{165}$ to enhance the collateral growth as suggested by the greater angiographic score. This could explain that in the CTGF-2 group, the maximal blood flow was restored in the ischemic limb compared with the non ischemic limb, but not in $VEGF_{165}$-treated animals.

This result strengthens the idea that a pleiotropic factor is more prone than an endothelium-specific mitogen to trigger arteriogenesis which is a complex morphogenic process. CTGF-2 may stimulate the revascularization by acting as an angiogenic inducer upon endothelial cells as VEGF does, and additionally by acting as a chemotactic, mitogenic and matrix remodeling factor upon fibroblasts[17,20]. Indeed, a potential function of CTGF-2 in matrix remodeling has been recently suggested through the activation of matrix metalloproteinases 1 and 3[29], enzymes known to play a role in angiogenesis. Involvement of CTGF-2 in angiogenesis can also be attributed to its interaction with different integrins: $\alpha v \beta_3$-dependent pathway for adhesion and migration of endothelial cells[19,20], $\alpha_6 \beta_1$ and $\alpha v \beta_3$ for adhesion and migration of fibroblasts, respectively[30]. Moreover, even if CTGF-2 is not mitogenic by itself, it may synergize with growth factors like bFGF to enhance mitogenesis of endothelial cells or fibroblasts[17,20,21].

Interestingly, CTGF2 angiogenic properties appears closely related to bFGF, with respect to induction of MMP-1 and MMP-3, to its interaction with integrin $\alpha v \beta_3$, implicated in bFGF-mediated angiogenesis[31], and also because bFGF, a major inducer of the CTGF-2 gene, has been presented as the main angiogenic factor implicated in arteriogenesis[28]. The interplay between the actions of bFGF and CTGF-2 is likely to be complex and remains to be more extensively investigated.

In conclusion, we have established that Ad-CTGF-2 gene transfer promotes a significant improvement of tissue perfusion in the ischemic limb. The results revealed that CTGF-2 appeared more prone to stimulate limb revascularization in comparison with $VEGF_{165}$, indicating that CTGF-2 is a useful as a therapeutic agent for treatment of severe peripheral ischemic disease.

REFERENCES FOR EXAMPLE 12

1. Bauters C, Asahara T, Zheng L P, Takeshita S, Bunting S, Ferrara N, Symes J F, Isner J M. Physiological assessment of augmented vascularity induced by VEGF in ischemic rabbit hindlimb. *Am J Physiol*. 1994;267:H1263–71.

2. Takeshita S, Weir L, Chen D, Zheng L P, Riessen R, Bauters C, Symes J F, Ferrara N, Isner J M. Therapeutic angiogenesis following arterial gene transfer of vascular endothelial growth factor in a rabbit model of hindlimb ischemia. *Biochem Biophys Res Commun*. 1996;227:628–35.

3. Rivard A, Silver M, Chen D, Kearney M, Magner M, Annex B, Peters K, Isner J M. Rescue of diabetes-related impairment of angiogenesis by intramuscular gene therapy with adeno-VEGF. *Am J Pathol*. 1999; 154:355–63.

4. Mack C A, Patel S R, Schwarz E A, Zanzonico P, Hahn R T, Ilercil A, Devereux R B, Goldsmith S J, Christian T F, Sanborn T A, Kovesdi I, Hackett N, Isom O W, Crystal R G, Rosengart T K. Biologic bypass with the use of adenovirus-mediated gene transfer of the complementary deoxyribonucleic acid for vascular endothelial growth factor 121 improves myocardial perfusion and function in the ischemic porcine heart. *J Thorac Cardiovasc Surg*. 1998; 115:168–76; discussion 176–7.

5. Witzenbichler B, Asahara T, Murohara T, Silver M, Spyridopoulos I, Magner M, Principe N, Kearney M, Hu J S, Isner J M. Vascular endothelial growth factor-C (VEGF-C/VEGF-2) promotes angiogenesis in the setting of tissue ischemia. *Am J Pathol*. 1998;153:381–94.

6. Garcia-Martinez C, Opolon P, Trochon V, Chianale C, Musset K, Lu H, Abitbol M, Perricaudet M, Ragot T. Angiogenesis induced in muscle by a recombinant adenovirus expressing functional isoforms of basic fibroblast growth factor. *Gene Ther*. 1999;6:1210–21.

7. Safi J, DiPaula A F, Riccioni T, Kajstura J, Ambrosio G, Becker L C, Anversa P, Capogrossi M C. Adenovirus-mediated acidic fibroblast growth factor gene transfer induces angiogenesis in the nonischemic rabbit heart. *Microvasc Res*. 1999;58:238–49.

8. Baumgartner I, Pieczek A, Manor O, Blair R, Kearney M, Walsh K, Isner J M. Constitutive expression of phVEGF165 after intramuscular gene transfer promotes collateral vessel development in patients with critical limb ischemia [see comments]. *Circulation*. 1998;97:1114–23.

9. Lazarous D F, Unger E F, Epstein S E, Stine A, Arevalo J L, Chew E Y, Quyyumi A A. Basic fibroblast growth factor in patients with intermittent claudication: results of a phase I trial. *J Am Coll Cardiol*. 2000;36:1239–44.

10. Hammond H K, McKirnan M D. Angiogenic gene therapy for heart disease: a review of animal studies and clinical trials. *Cardiovasc Res*. 2001;49:561–7.

11. Lau L F, Lam S C. The CCN family of angiogenic regulators: the integrin connection. *Exp Cell Res*. 1999;248:44–57.

12. Brunner A, Chinn J, Neubauer M, Purchio A F. Identification of a gene family regulated by transforming growth factor-beta. *DNA Cell Biol*. 1991;10:293–300.

13. Lau L F, Nathans D. Identification of a set of genes expressed during the G0/G1 transition of cultured mouse cells. *Embo J*. 1985;4:3145–51.

14. Lau L F, Nathans D. Expression of a set of growth-related immediate early genes in BALB/c 3T3 cells: coordinate regulation with c-fos or c-myc. *Proc Natl Acad Sci USA*. 1987;84:1182–6.

15. O'Brien T P, Yang G P, Sanders L, Lau L F. Expression of cyr61, a growth factor-inducible immediate-early gene. *Mol Cell Biol*. 1990;10:3569–77.

16. Yang G P, Lau L F. Cyr61, product of a growth factor-inducible immediate early gene, is associated with the extracellular matrix and the cell surface. *Cell Growth Differ*. 1991;2:351–7.

17. Kireeva M L, Mo F E, Yang G P, Lau L F. Cyr61, a product of a growth factor-inducible immediate-early gene, promotes cell proliferation, migration, and adhesion. *Mol Cell Biol*. 1996;16:1326–34.

18. Kireeva M L, Latinkic B V, Kolesnikova T V, Chen C C, Yang G P, Abler A S, Lau L F. Cyr61 and Fisp12 are both ECM-associated signaling molecules: activities, metabolism, and localization during development. *Exp Cell Res*. 1997;233:63–77.

19. Kireeva M L, Lam S C, Lau L F. Adhesion of human umbilical vein endotbelial cells to the immediate-early gene product Cyr61 is mediated through integrin alphavbeta3. *J Biol Chem*. 1998;273:3090–6.

20. Babic A M, Kireeva M L, Kolesnikova T V, Lau L F. CYR61, a product of a growth factor-inducible immediate early gene, promotes angiogenesis and tumor growth. *Proc Natl Acad Sci USA*. 1998;95:6355–60.

21. Kolesnikova T V, Lau L F. Human CYR61-mediated enhancement of bFGF-induced DNA synthesis in human umbilical vein endothelial cells. *Oncogene*. 1998;16:747–54.

22. Pu L Q, Sniderman A D, Brassard R, Lachapella K J. Enhanced revascularization of the ischemic limb by angiogenic therapy. *Circulation*. 1993;88:208–15.

23. Chartier C, Degryse E, Gantzer M, Dieterle A, Pavirani A, Mehtali M. Efficient generation of recombinant adenovirus vectors by homologous recombination in *Escherichia coli. J Virol*. 1996;70:4805–10.

24. Lusky M, Christ M, Rittner K, Dieterle A, Dreyer D, Mourot B, Schultz H, Stoeckel F, Pavirani A, Mehtali M. In vitro and in vivo biology of recombinant adenovirus vectors with E1, E1/E2A, or E1/E4 deleted. *J Virol*. 1998;72:2022–32.

25. Ziada A M, Hudlicka O, Tyler K R, Wright A J. The effect of long-term vasodilatation on capillary growth and performance in rabbit heart and skeletal muscle. *Cardiovasc Res*. 1984;18:724–32.

26. Baffour R, Achanta K, Kauftnan J, Berman J, Garb J L, Rhee S, Friedmann P. Synergistic effect of basic fibroblast growth factor and methylprednisolone on neurological function after experimental spinal cord injury. *J Neurosurg*. 1995;83:105–10.

27. Takeshita S, Zheng L P, Brogi E, Kearney M, Pu L Q, Bunting S, Ferrara N, Symes J F, Isner J M. Therapeutic angiogenesis. A single intraarterial bolus of vascular endothelial growth factor augments revascularization in a rabbit ischemic hind limb model. *J Clin Invest*. 1994;93:662–70.

28. Arras M, Ito W D, Scholz D, Winkler B, Schaper J, Schaper W. Monocyte activation in angiogenesis and collateral growth in the rabbit hindlimb. *J Clin Invest*. 1998;101:40–50.

29. Chen C C, Chen N, Lau L F. The angiogenic factors Cyr61 and CTGF induce adhesive signaling in primary human skin fibroblasts. *J Biol Chem*. 2000; 18:18.

30. Grzeszkiewicz T M, Kirschling D J, Chen N, Lau L F. CYR61 stimulates human skin fibroblast migration through integrin {alpha} V{beta} 5 and enhances mitogenesis through integrin {alpha} V {beta} 3, independent of its carboxy-terminal domain. *J Biol Chem*. 2001;3:3.

31. Friedlander M, Brooks P C, Shaffer R W, Kincaid C M, Varner J A, Cheresh D A. Definition of two angiogenic pathways by distinct alpha v integrins. *Science*. 1995;270:1500–2.

Numerous modifications and variations of the present invention are possible in light of the above teachings and, therefore, within the scope of the appended claims, the invention may be practiced otherwise than as particularly described.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

Certain CTGF-2 polynucleotides and polypeptides of the present invention, including antibodies, were disclosed in U.S. provisional application Nos. 60/217,402, filed Jul. 11, 2000, and 60/291,642, filed May 18, 2001, the specifications and sequence listings of which are herein incorporated by reference in their entireties.

---

What is claimed is:

1. A method of stimulating angiogenesis in a mammal, comprising intramuscularly administering to said mammal an effective amount of adenoviral vector pTG14550 (Pasteur Institute Deposit Number CNCM I-2695).

2. The method of claim 1, wherein the mammal has ischemia.

3. The method of claim 1, wherein the mammal is treated for limb revascularization.

4. The method of claim 3, wherein the limb is a leg.

5. The method of claim 3, wherein the limb is an arm.

6. The method of claim 1, wherein the mammal is human.

7. The method of claim 1, wherein the adenoviral vector is administered with a pharmaceutically acceptable carrier selected from the group consisting of:
   (a) saline,
   (b) buffered saline,
   (c) dextrose,
   (d) water,
   (e) glycerol,
   (f) ethanol, and
   (g) combinations of the above.

8. A method of treating ischemia in a mammal, comprising intramuscularly administering to said mammal an effective amount of adenoviral vector pTG14550 (Pasteur Institute Deposit Number CNCM I-2695).

9. The method of claim 8, wherein the adenoviral vector is administered with a pharmaceutically acceptable carrier selected from the group consisting of:
   (a) saline,
   (b) buffered saline,
   (c) dextrose,
   (d) water,
   (e) glycerol,
   (f) ethanol, and
   (g) combinations of the above.

10. A method of stimulating the migration of human dermal microvascular endothelial cells (HDMEC), comprising contacting said cells with an effective amount of adenoviral vector pTG14550 (Pasteur Institute Deposit Number CNCM I-2695).

11. The method of claim 10, wherein said contacting is performed in vitro.

* * * * *

SEQUENCE LISTING

```
<160> NUMBER OF SEQ ID NOS: 8

<210> SEQ ID NO 1
<211> LENGTH: 1146
<212> TYPE: DNA
<213> ORGANISM: homo sapiens

<400> SEQUENCE: 1
atgagctccc gcatcgccag ggcgctcgcc ttagtcgtca cccttctcca cttgaccagg      60
ctggcgctct ccacctgccc cgctgcctgc cactgccccc tggaggcgcc caagtgcgcg     120
ccgggagtcg ggctggtccg ggacggctgc ggctgctgta aggtctgcgc caagcagctc     180
aacgaggact gcagcaaaac gcagccctgc gaccacacca aggggctgga atgcaacttc     240
ggcgccagct ccaccgctct gaaggggatc tgcagagctc agtcagaggg cagaccctgt     300
gaatataact ccagaatcta ccaaaacggg gaaagtttcc agcccaactg taaacatcag     360
tgcacatgta ttgatggcgc cgtgggctgc attcctctgt gtcccccaaga actatctctc     420 cccaacttgg gctgtcccaa ccctcggctg gtcaaagtta ccgggcagtg ctgcgaggag     480
tgggtctgtg acgaggatag tatcaaggac cccatggagg accaggacgg cctccttggc     540
aaggagctgg gattcgatgc ctccgaggtg gagttgacga gaaacaatga attgattgca     600
gttggaaaag gcagctcact gaagcggctc cctgtttttg gaatggagcc tcgcatccta     660
```

-continued

```
tacaacccttt tacaaggcca gaaatgtatt gttcaaacaa cttcatggtc ccagtgctca    720
aagacctgtg gaactggtat ctccacacga gttaccaatg acaaccctga gtgccgcctt    780
gtgaaagaaa cccggatttg tgaggtgcgg ccttgtggac agccagtgta cagcagcctg    840
aaaaagggca agaaatgcag caagaccaag aaatcccccg aaccagtcag gtttacttac    900
gctggatgtt tgagtgtgaa gaaataccgg cccaagtact gcggttcctg cgtggacggc    960
cgatgctgca cgccccagct gaccaggact gtgaagatgc ggttccgctg cgaagatggg   1020
gagacatttt ccaagaacgt catgatgatc cagtcctgca atgcaactaa caactgcccg   1080
catgccaatg aagcagcgtt tcccttctac aggctgttca atgacattca caaatttagg   1140
gactaa                                                              1146
```

<210> SEQ ID NO 2
<211> LENGTH: 381
<212> TYPE: PRT
<213> ORGANISM: homo sapiens

<400> SEQUENCE: 2

```
Met Ser Ser Arg Ile Ala Arg Ala Leu Ala Leu Val Val Thr Leu Leu
  1               5                  10                  15

His Leu Thr Arg Leu Ala Leu Ser Thr Cys Pro Ala Ala Cys His Cys
             20                  25                  30

Pro Leu Glu Ala Pro Lys Cys Ala Pro Gly Val Gly Leu Val Arg Asp
         35                  40                  45

Gly Cys Gly Cys Cys Lys Val Cys Ala Lys Gln Leu Asn Glu Asp Cys
     50                  55                  60

Ser Lys Thr Gln Pro Cys Asp His Thr Lys Gly Leu Glu Cys Asn Phe
 65                  70                  75                  80

Gly Ala Ser Ser Thr Ala Leu Lys Gly Ile Cys Arg Ala Gln Ser Glu
                 85                  90                  95

Gly Arg Pro Cys Glu Tyr Asn Ser Arg Ile Tyr Gln Asn Gly Glu Ser
            100                 105                 110

Phe Gln Pro Asn Cys Lys His Gln Cys Thr Cys Ile Asp Gly Ala Val
        115                 120                 125

Gly Cys Ile Pro Leu Cys Pro Gln Glu Leu Ser Leu Pro Asn Leu Gly
    130                 135                 140

Cys Pro Asn Pro Arg Leu Val Lys Val Thr Gly Gln Cys Cys Glu Glu
145                 150                 155                 160

Trp Val Cys Asp Glu Asp Ser Ile Lys Asp Pro Met Glu Asp Gln Asp
                165                 170                 175

Gly Leu Leu Gly Lys Glu Leu Gly Phe Asp Ala Ser Glu Val Glu Leu
            180                 185                 190

Thr Arg Asn Asn Glu Leu Ile Ala Val Gly Lys Gly Ser Ser Leu Lys
        195                 200                 205

Arg Leu Pro Val Phe Gly Met Glu Pro Arg Ile Leu Tyr Asn Pro Leu
    210                 215                 220

Gln Gly Gln Lys Cys Ile Val Gln Thr Thr Ser Trp Ser Gln Cys Ser
225                 230                 235                 240

Lys Thr Cys Gly Thr Gly Ile Ser Thr Arg Val Thr Asn Asp Asn Pro
                245                 250                 255

Glu Cys Arg Leu Val Lys Glu Thr Arg Ile Cys Glu Val Arg Pro Cys
            260                 265                 270

Gly Gln Pro Val Tyr Ser Ser Leu Lys Lys Gly Lys Lys Cys Ser Lys
```

```
                   275                 280                 285
        Thr Lys Lys Ser Pro Glu Pro Val Arg Phe Thr Tyr Ala Gly Cys Leu
            290                 295                 300

Ser Val Lys Lys Tyr Arg Pro Lys Tyr Cys Ser Cys Val Asp Gly
        305                 310                 315                 320

Arg Cys Cys Thr Pro Gln Leu Thr Arg Thr Val Lys Met Arg Phe Arg
                        325                 330                 335

Cys Glu Asp Gly Glu Thr Phe Ser Lys Asn Val Met Met Ile Gln Ser
                        340                 345                 350

Cys Lys Cys Asn Tyr Asn Cys Pro His Ala Asn Glu Ala Ala Phe Pro
                        355                 360                 365

Phe Tyr Arg Leu Phe Asn Asp Ile His Lys Phe Arg Asp
        370                 375                 380

<210> SEQ ID NO 3
<211> LENGTH: 28
<212> TYPE: DNA
<213> ORGANISM: homo sapiens

<400> SEQUENCE: 3
cgcgggatcc tgcgcgacac aatgagct                                              28

<210> SEQ ID NO 4
<211> LENGTH: 27
<212> TYPE: DNA
<213> ORGANISM: homo sapiens

<400> SEQUENCE: 4
aaaggatcca caatgagctc ccgaatc                                               27

<210> SEQ ID NO 5
<211> LENGTH: 58
<212> TYPE: DNA
<213> ORGANISM: homo sapiens

<400> SEQUENCE: 5
cgctctagat taagcgtagt ctgggacgtc gtatgggtat tggaacagcc tgtagaag            58

<210> SEQ ID NO 6
<211> LENGTH: 1128
<212> TYPE: DNA
<213> ORGANISM: homo sapiens

<400> SEQUENCE: 6
atgagctccc gaatcgtcag ggagctcgcc ttagtcgtca cccttctcca cttgaccagg          60
gtggggctct ccacctgccc cgctgactgc cactgccccc tggaggcgcc caagtgcgcg         120
ccgggagtcg ggctggtccg ggacggctgc ggctgttgta aggtctgcgc caagcagctc         180
aacgaggact gcagaaaaac gcagccctgc gaccacacca gggggctgga atgcaacttc         240
ggcgccagct ccaccgctct gaaggggatc tgcagagctc agtcagaggg cagaccctgt         300
gaatataact ccagaatcta ccaaaacggg aaagtttccc agcccaactg taaacatcag         360
tgcacatgta ttggatggcg ccgggggggct tgcattcctc tgtgtcccca agaactatct       420
ctccccaact gggctgtccc aacccctcgg ctggtcaaag ttaccgggca gtgctgcgag         480
gagtgggtct gtgacgagga gtatcaaga cccccatgg aggaccagga cggcctcctt           540
ggcaaggggc tgggattcga tgcctccgag gtggagttga cgagaaacaa tgaattgatt         600
gcagttggaa aaggcagctc actgaagcgg ctccctgttt ttggaatgga gcctcgcatc         660
```

-continued

```
ctatacaacc ctttacaagg ccagaaatgt attgttcaaa caacttcatg gtcccagtgc      720
tcaaagacct gtggaactgg tatctccaca cgagttacca atgacaaccc tgagtgccgc      780
cttgtgaaag aaacccggat ttgtgaggtg cggccttgtg acagccagt gtacagcagc       840 ctgaaaaagg gcaagaaatg cagcaagacc aagaaatccc ccgaaccagt caggtttact     900
tacgctggat gtttgagtgt gaagaaatac cggcccaagt actgcggttc ctgcgtggac      960
ggccgatgct gcacgcccca gctgaccagg actgtgaaga tgcggttccc ctgcgaagat    1020
ggggagacat tttccaagaa cgtcatgatg atccagtcct ccaaatgcaa ctacaactgc    1080
ccgcatgcca atgaagcagc gtttcccttc tacaggctgt tccaatga                  1128
```

<210> SEQ ID NO 7
<211> LENGTH: 375
<212> TYPE: PRT
<213> ORGANISM: homo sapiens

<400> SEQUENCE: 7

```
Met Ser Ser Arg Ile Val Arg Glu Leu Ala Leu Val Val Thr Leu Leu
1               5                   10                  15

His Leu Thr Arg Val Gly Leu Ser Thr Cys Pro Ala Asp Cys His Cys
                20                  25                  30

Pro Leu Glu Ala Pro Lys Cys Ala Pro Gly Val Gly Leu Val Arg Asp
            35                  40                  45

Gly Cys Gly Cys Cys Lys Val Cys Ala Lys Gln Leu Asn Glu Asp Cys
        50                  55                  60

Arg Lys Thr Gln Pro Cys Asp His Thr Lys Gly Leu Glu Cys Asn Phe
65                  70                  75                  80

Gly Ala Ser Ser Thr Ala Leu Lys Gly Ile Cys Arg Ala Gln Ser Glu
                85                  90                  95

Gly Arg Pro Cys Glu Tyr Asn Ser Arg Ile Tyr Gln Asn Gly Glu Ser
            100                 105                 110

Phe Gln Pro Asn Cys Lys His Gln Cys Thr Cys Ile Gly Trp Arg Arg
        115                 120                 125

Gly Ala Cys Ile Pro Leu Cys Pro Gln Glu Leu Ser Leu Pro Asn Leu
    130                 135                 140

Gly Cys Pro Asn Pro Arg Leu Val Lys Val Thr Gly Gln Cys Cys Glu
145                 150                 155                 160

Glu Trp Val Cys Asp Glu Asp Ser Ile Lys Asp Pro Met Glu Asp Gln
                165                 170                 175

Asp Gly Leu Leu Gly Lys Gly Leu Gly Phe Asp Ala Ser Glu Val Glu
            180                 185                 190

Leu Thr Arg Asn Asn Glu Leu Ile Ala Val Gly Lys Gly Ser Ser Leu
        195                 200                 205

Lys Arg Leu Pro Val Phe Gly Met Glu Pro Arg Ile Leu Tyr Asn Pro
    210                 215                 220

Leu Gln Gly Gln Lys Cys Ile Val Gln Thr Thr Ser Trp Ser Gln Cys
225                 230                 235                 240

Ser Lys Thr Cys Gly Thr Gly Ile Ser Thr Arg Val Thr Asn Asp Asn
                245                 250                 255

Pro Glu Cys Arg Leu Val Lys Glu Thr Arg Ile Cys Glu Val Arg Pro
            260                 265                 270

Cys Gly Gln Pro Val Tyr Ser Ser Leu Lys Lys Gly Lys Lys Cys Ser
        275                 280                 285
```

-continued

```
Lys Thr Lys Lys Ser Pro Glu Pro Val Arg Phe Thr Tyr Ala Gly Cys
    290             295             300

Leu Ser Val Lys Lys Tyr Arg Pro Lys Tyr Cys Gly Ser Cys Val Asp
305             310             315             320

Gly Arg Cys Cys Thr Pro Gln Leu Thr Arg Thr Val Lys Met Arg Phe
            325             330             335

Pro Cys Glu Asp Gly Glu Thr Phe Ser Lys Asn Val Met Met Ile Gln
            340             345             350

Ser Ser Lys Cys Asn Tyr Asn Cys Pro His Ala Asn Glu Ala Ala Phe
            355             360             365

Pro Phe Tyr Arg Leu Phe Gln
    370             375

<210> SEQ ID NO 8
<211> LENGTH: 30
<212> TYPE: DNA
<213> ORGANISM: homo sapiens

<400> SEQUENCE: 8
cgcgggtacc aggtagcatt tagtccctaa                                        30
```